US 6,682,924 B1

United States Patent
Sierkstra et al.

(10) Patent No.: US 6,682,924 B1
(45) Date of Patent: *Jan. 27, 2004

(54) PROTEASE VARIANTS AND COMPOSITIONS

(75) Inventors: Laurens Nicolaas Sierkstra, Delft (NL); Jan Klugkist, Vlaardingen (NL); Peter Markvardsen, Bagsværd (DK); Claus von der Osten, Lyngby (DK); Peter Bauditz, Koebenhavn OE (DK)

(73) Assignees: Novozymes A/S, Bagsvaerd (DK); Unilever, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/587,747

(22) Filed: Jun. 5, 2000

Related U.S. Application Data

(63) Continuation of application No. 09/120,577, filed on Jul. 22, 1998, now Pat. No. 6,190,900, which is a continuation of application No. 08/642,987, filed on May 6, 1996, now Pat. No. 5,837,517.

(30) Foreign Application Priority Data

May 5, 1995 (DK) .............................................. 0519/95
May 5, 1995 (EP) .............................................. 95201161
Apr. 12, 1996 (DK) .............................................. 0421/96

(51) Int. Cl.[7] .......................... C12N 9/54; C12N 15/57; C12N 15/74; C11D 3/386
(52) U.S. Cl. ...................... 435/220; 435/69.1; 435/221; 435/222; 435/252.31; 435/320.1; 435/471; 536/23.2
(58) Field of Search ................................. 435/220, 221, 435/222, 69.1, 471

(56) References Cited

U.S. PATENT DOCUMENTS 4,980,288 A * 12/1990 Bryan et al. ................. 435/219
5,116,741 A * 5/1992 Bryan et al. .................. 435/87

(List continued on next page.)

FOREIGN PATENT DOCUMENTS

| EP | 0251466 A2 | * | 1/1988 |
| EP | 0 405 901 A1 | | 1/1991 |
| EP | 0 525 610 A2 | | 2/1993 |
| EP | 0357157 A1 | * | 1/1998 |
| WO | WO 88/08028 A1 | * | 10/1988 |
| WO | WO 89/06279 | | 7/1989 |
| WO | WO 89/07642 A1 | * | 8/1989 |
| WO | WO 91/00345 | | 1/1991 |
| WO | WO 92/08778 A1 | * | 5/1992 |
| WO | WO 92/11357 A1 | * | 7/1992 |
| WO | WO 92/21760 A1 | * | 12/1992 |
| WO | WO 94/02618 A1 | * | 2/1994 |

Primary Examiner—Ponnathapu Achutamurthy
Assistant Examiner—William W. Moore
(74) Attorney, Agent, or Firm—Elias J. Lambiris

(57) ABSTRACT

The present invention relates to enzymes produced by mutating the genes for a number of subtilases and expressing the mutated genes in suitable hosts are presented. The enzymes exhibit improved stability and/or improved wash performance in any detergent in comparison to their wild type parent enzymes. The enzymes are well-suited for use in any detergent and for some in especially liquid or solid shaped detergent compositions.

60 Claims, 2 Drawing Sheets

U.S. PATENT DOCUMENTS

| | | | |
|---|---|---|---|
| 5,324,653 A | * 6/1994 | van Eekelen et al. | 435/221 |
| 5,336,611 A | * 8/1994 | van Eekelen et al. | 435/221 |
| 5,340,735 A | * 8/1994 | Christianson et al. | 435/221 |
| 5,352,603 A | * 10/1994 | Vetter et al. | 435/221 |
| 5,389,307 A | * 2/1995 | Lindegaard et al. | 252/549 |
| 5,453,372 A | * 9/1995 | Vetter et al. | 435/222 |
| 5,482,849 A | * 1/1996 | Branner et al. | 435/222 |
| 5,500,364 A | * 3/1996 | Christianson et al. | 435/221 |
| 5,631,217 A | * 5/1997 | Branner et al. | 510/320 |
| 5,665,587 A | * 9/1997 | Aaslyng et al. | 435/221 |
| 5,700,676 A | * 12/1997 | Bott et al. | 435/221 |
| 5,741,288 A | * 4/1998 | Hastrup et al. | 435/221 |
| 5,801,039 A | * 9/1998 | Maurer et al. | 435/221 |
| 6,197,567 B1 | * 3/2001 | Aaslyng et al. | 435/221 |
| 6,197,589 B1 | * 3/2001 | Maurer et al. | 435/471 |
| 6,287,841 B1 | * 9/2001 | Mulleners et al. | 435/221 |

* cited by examiner

FIG. 1

```
               130            140                    160              170       180      190              200
                -              -                      -                -         -        -                -
BASBPN  GGPSG------------SAAL KAAVDKAVAS--EGTSGSSS-----------------TVGYPGKYP--FSS-------VGPE------LDVMAP
BSS168  GGPTG------------STAL KTVDKAVSS---EGSSGSTS-----------------TVGYPAKYP--FSS-------AGSE------LDVMAP
BSSDY   GGPSG------------STAL KQAVDKAYAS--SGSSGSQN-----------------TIGYPAKYD--FSS-------VGAE------LEVMAP
BLSCAR  GGPSG------------STAM KQAVONAYAR--SGSSGNTN-----------------TIGYPAKYD--FSS-------VGAE------LEVMAP
BAPB92  GSPSP------------SATI EQAVNSATSR--SGAG--------------------SISYPARYA--FSQ-------YGAG------LDIVAP
BYSYAB  GSSAG------------SATM EQAVNQATAS--SGAG--------------------NVGFPARYA--FSQ-------YGAG------LDIVAP
BLS147  GSTSG------------SSTL ELAVRRANNA--TGRQ--------------------GVNYPARYS--FST-------YGPE------IEISAP
BSEPR   GTTSD------------SKIL HDAVNKAYEQ--DGNGK--------------------PVNYPAAYS--FST-------TCDE------VEFSAP
BSISP1  CGPSD------------VPEL EEAVKNAVKN--EGDGDERTE-----------------ELSYPAAYN--FSN-------ANKE------IDLVAP
TVTHER  GGTVG------------NSGL QQAVNYAHNX--AGNT---------------------APNYPAYYS--FST-------YGSW------VDVAAP
DNEBPR  GGGGG------------CSQNS QRMIDKTTNL--ENQQA--------------------SRTWPSSCN--FSN-------YGAR------VHLAAP
XCEXPR  GGGGS------------CSTTM QNAINGAVSR--QASNV--------------------SGSLPANCA--YSN-------FGTG------IDVSAP
BSBPF   GGGSG------------LDEWY RDMVNAWRAA--TDLFIPGGPG---------------SIANPANYP--FGL-------QGPSPYDEIKPEISAP
EFCYLA  GSYKN------------MEIDDERFTVEAF RKVVNYARKN--ESRDISTGN---------------EKHIPGGLE--YSN-------YGSN------VSIYGP
SEEPIP  GNYLI-(9)-RDDEKVDYDAL QKAINYAQKK--DGIHVKKVKEINKKR(5)TSKKVYDSPANLN--FSN-------YGNH------FIDLMTI
SPSCPA  GNAAL------------AYANLPDET KKAFDYAKSK--DSSFGGKTRLPLAD--HPDYGVVGTPAAAD--FSS-------NGLTAOGNIKPDIAAP
LLSKI1  GSNSG------------NQTLEDPE LAAVQNAHES--SGTSGSATEGVNKDYYGLQDNEMVGSPGTSR--FTS-------YGPVSNLSFKPDITAP
SMEXSP  GIAPD-(4)--QPVPTGGHSA HSTLLRAARH--YNNYNIPEAQKSL-----------PYAFPDVLH--SST-------SCGQTAS---YCVSAP
AVPRCA  GPPDG-(10)-KQKVPLPDST RLAHDYAINKG  GNESVD-------------NDGYASYEK--YSD-------FGTA------VWCAFF
HMPPCJ  GPNDD------------GKTVEGPGRLA QKAFEYGVKQG  GGRQGDNCD-------------CDGYTDSIY--YAE-------KCSS------TLATSY
HSIPC2  GPTDN------------GKTVDGPROVT LQAMADGVNKG  GGSY--QDCN-------------CDGYASSMW--YDE-------SCSS------TLASTF
HSFURI  GPEDD------------CKTVDGPARLA EEAFFRGVSQG  GGRENDSCN-------------CDGYTNSIY--YSE-------ACSS------TLATTY
DMFUR1  GPDDD------------GKTVDGPGELA SRAFIEGTTKG  GGREQDNCN-------------CDGYTNSIW--YSE-------KCSS------TLATTY
KLKEX1  GPSDD------------GKTMQAPDTLV KKAIIKGVTEG  GGMFGDSCN-------------FDGYTNSIF--YSE-------SCSA------VHVVTY
SCKEX2  GPADD------------GRHLQGPSDLV KKALVKGVTEG  GGTRGDNCN-------------YDGYTNSIY--YSE-------GCSA------VHAVTY

VAPROA  GGGQS------------VALDSAVQSAVQS--SNA--DACN-----------------YSPARVA--FSN-------WGSC------VDVFAP
TRT41A  GGGAS------------TALDTAVHNAINA--DNR--DACF-----------------YSPARVT--FSN-------YGRC------LDLFAP
TAAQUA  GGGVS------------TALDNAVKHSIAA--DHA--NACN-----------------YSPARVA--FSN-------YGSC------VDLFAP
TAPROK  GGGYS------------SSVNSAAARLQSS--NHA--DARN-----------------YSPASEP--FSN-------YGSV------LDIFGP
TAPROR  GGGYS------------SSVNSAAAMLQQS--NHA--DARN-----------------YSPASES--FSN-------YGSV------LDIFAP
TAPROT  GGPSS------------SAVNRAAAEITSA--EAT--DASS-----------------SSPASEE--YSN-------FGSV------VDLLAP
ACALPR  GGGYS------------SAFNNAVHTAYSR--DNQ--HAAN-----------------YSPASAA--FSII------YGSV------LDIFAP
AOALPR  GGGYS------------KAFNDAVENAFEQ--ENS--DAGQ-----------------TSPASAP--FSN-------FGKV------VDVFAP
SCPRB1  GGGKS------------PALDLAVNAAVEV--ENQ--DACN-----------------TSPASAD--FSN-------NGKC------VDVFAP
YLXPR2  GGPKS------------ASQDALWSRATQE--DAV--DACN-----------------DSPGNIGGWSGGQGSNYGTC------VDVFAP
```

PROTEASE VARIANTS AND COMPOSITIONS

CROSS-REFERENCE TO RELATED APPLICATIONS

This application is a continuation of U.S. Ser. No. 09/120, 577, which has issued as U.S. Pat. No. 6,190,900 filed Jul. 22, 1998, which is a continuation of U.S. Ser. No. 08/642, 987, which has issued as U.S. Pat. No. 5,837,517 filed May 6, 1996, and claims priority under 35 U.S.C. 119 of Danish application no. 0421/96 filed on Apr. 12, 1996, Danish application no. 0519/95 filed on May 5, 1995, and European application no. 95201161.7 filed on May 5, 1995, the contents of which are fully incorporated herein by reference.

TECHNICAL FIELD

This invention relates to novel mutant enzymes or enzyme variants useful in formulating detergent compositions and exhibiting improved storage stability while retaining or improving their wash performance; cleaning and detergent compositions containing said enzymes; mutated genes coding for the expression of said enzymes when inserted into a suitable host cell or organism; and such host cells transformed therewith and capable of expressing said enzyme variants.

BACKGROUND OF THE INVENTION

In the detergent industry enzymes have for more than 30 years been implemented in washing formulations. Enzymes used in such formulations comprise proteases, lipases, amylases, cellulases, as well as other enzymes, or mixtures thereof. Commercially most important are proteases.

Although proteases have been used in the detergent industry for more than 30 years, much remains unknown as to details of how these enzymes interact with substrates and/other substances present in e.g. detergent compositions. Some factors related to specific residues and influencing certain properties, such as oxidative and thermal stability in general have been elucidated, but much remains to be found out. Also, it is still not exactly known which physical or chemical characteristics are responsible for a good washing performance or stability of a protease in a specific detergent composition.

The currently used proteases have for the most part been found by isolating proteases from nature and testing them in detergent formulations.

An increasing number of commercially used protease are protein engineered variants of the corresponding naturally occurring wild type protease, e.g. DURAZYM® (Novo Nordisk A/S), RELASE® (Novo Nordisk A/S), MAX-APEM® (Gist-Brocades N.V.), PURAFECT® (Genencor International, Inc.).

Therefore, an object of the present invention, is to provide improved protein engineered protease variants, especially for use in the detergent industry.

PROTEASES

Enzymes cleaving the amide linkages in protein substrates are classified as proteases, or (interchangeably) peptidases (see Walsh, 1979, *Enzymatic Reaction Mechanisms*. W.H. Freeman and Company, San Francisco, Chapter 3). Bacteria of the Bacillus species secrete two extracellular species of protease, a neutral, or metalloprotease, and an alkaline protease which is functionally a serine endopeptidase and usually referred to as subtilisin. Secretion of these proteases has been linked to the bacterial growth cycle, with greatest expression of protease during the stationary phase, when sporulation also occurs. Joliffe et al. (1980) *J. Bacteriol* 141 1199–1208, have suggested that Bacillus proteases finction in cell wall turnover.

SUBTILASES

A serine protease is an enzyme which catalyzes the hydrolysis of peptide bonds, and in which there is an essential serine residue at the active site (White, Handler and Smith, 1973 *"Principles of Biochemistry,"* Fifth Edition, McGraw-Hill Book Company, NY, pp. 271–272).

The bacterial serine proteases have molecular weights in the 20,000 to 45,000 Daltons range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) *Bacteriological Rev.* 41 711–753).

A sub-group of the serine proteases tentatively designated subtilases has been proposed by Siezen et al., *Protein Engng.* 4 (1991) 719–737. They are defined by homology analysis of more than 40 amino acid sequences of serine proteases previously referred to as subtilisin-like proteases. A subtilisin was previously defined as a serine protease produced by Gram-positive bacteria or fungi, and according to Siezen et al. now is a subgroup of the subtilases. A wide variety of subtilisins have been identified, and the amino acid sequence of a number of subtilisins have been determined. These include more than six subtilisins from Bacillus strains, namely, subtilisin 168, subtilisin BPN', subtilisin Carlsberg, subtilisin Y, subtilisin amylosacchariticus, and mesentericopeptidase (Kurihara et al. (1972) *J. Biol. Chem.* 247 5629–5631; Wells et al. (1983) *Nucleic Acids Res.* 11 7911–7925; Stahl and Ferrari (1984) *J. Bacteriol.* 159 811–819, Jacobs et al. (1985) *Nucl. Acids Res.* 13 8913–8926; Nedkov et al. (1985) *Biol. Chem. Hoppe-Seyler* 366 421–430, Svendsen et al. (1986) *FEBS Lett.* 196 228–232), one subtilisin from an actinomycetales, thermitase from *Thermoactinomyces vulgaris* (Meloun et al. (1985) *FEBS Lett.* 198 195–200), and one fungal subtilisin, proteinase K from *Tritirachium album* (Jany and Mayer (1985) *Biol. Chem. Hoppe-Seyler* 366 584–492). for further reference Table I from Siezen et al. has been reproduced below.

Subtilisins are well-characterized physically and chemically. In addition to knowledge of the primary structure (amino acid sequence) of these enzymes, over 50 high resolution X-ray structures of subtilisins have been determined which delineate the binding of substrate, transition state, products, at least three different protease inhibitors, and define the structural consequences for natural variation (Kraut (1977) *Ann. Rev. Biochem.* 46 331–358).

In the context of this application substrate should be interpreted in its broadest form as comprising a compound containing at least one peptide bond susceptible to hydrolysis by a subtilisin protease.

Also the expression "product" should in the context of this invention be interpreted to include the products of a hydrolysis reaction involving a subtilisin protease. A product may be the substrate in a subsequent hydrolysis reaction.

One subgroup of the subtilases, I-S1, comprises the "classical" subtilisins, such as subtilisin 168, subtilisin BPN', subtilisin Carlsberg (ALCALASE®, Novo Nordisk A/S), and subtilisin DY.

A further subgroup of the subtilases I-S2, is recognised by Siezen et al. (supra). Sub-group I-S2 proteases are described as highly alkaline subtilisins and comprise enzymes such as subtilisin PB92 (MAXACAL®, Gist-Brocades N.V., subtilisin 309 (SAVINASE®, Novo Nordisk A/S), subtilisin 147 (ESPERASE®, Novo Nordisk A/S), and alkaline elastase YaB.

In the context of this invention, a subtilase variant or mutated subtilase means a subtilase that has been produced by an organism which is expressing a mutant gene derived from a parent microorganism which possessed an original or parent gene and which produced a corresponding parent enzyme, the parent gene having been mutated in order to produce the mutant gene from which said mutated subtilisin protease is produced when expressed in a suitable host.

Random and site-directed mutations of the subtilase gene have both arisen from knowledge of the physical and chemical properties of the enzyme and contributed information relating to subtilase's catalytic activity, substrate specificity, tertiary structure, etc. (Wells et al. (1987) *Proc. Natl. Acad. Sci. USA.* 84; 1219–1223; Wells et al. (1986) *Phil. Trans. R. Soc. Lond.A.* 317 415–423; Hwang and Warshel (1987) *Biochem.* 26 2669–2673; Rao et al., (1987) *Nature* 328 551–554.

More recent publications covering this area are Carter et al. (1989) *Proteins* 6 240–248 relating to design of variants that cleave a specific target sequence in a substrate (positions 24 and 64); Graycar et al. (1992) *Annals of the New York Academy of Sciences* 672 71–79 discussing a number of previously published results; and Takagi (1993) *Int. J. Biochem.* 25 307–312 also reviewing previous results.

Especially site-directed mutagenesis of the subtilisin genes has attracted much attention, and various mutations are described in the following patent applications and patents:

EP 130 756 (Genentech) (corresponding to U.S. Reissue Patent No. 34,606 (Genencor)) relating to site specific or randomly generated mutations in "carbonyl hydrolases" and subsequent screening of the mutated enzymes for various properties, such as $k_{cat}/K_m$ ratio, pH-activity profile, and oxidation stability. This publication reveals that site-specific mutation is feasible, and that mutation of subtilisin BPN' in certain specified positions, i.e. $^{-1}$Tyr, $^{32}$Asp, $^{155}$Asn, $^{104}$Tyr, $^{222}$Met, $^{166}$Gly, $^{64}$His, $^{169}$Gly, $^{189}$Phe, $^{33}$Ser, $^{221}$Ser, $^{217}$Tyr, $^{156}$Glu or $^{152}$Ala, provide for enzymes exhibiting altered properties. Since these positions all except position −1 were known to be involved in the functioning of the enzyme prior to the filing of the application, and therefore evident to select, this application does not contribute much to solving the problem of deciding where to introduce mutations in order to obtain enzymes with desired properties.

EP 214 435 (Henkel) relating to cloning and expression of subtilisin Carlsberg and two mutants thereof. In this application no reason for mutation of $^{158}$Asp to $^{158}$Ser and $^{161}$Ser to $^{161}$Asp is provided.

In International patent publication No. WO 87/04461 (Amgen) it is proposed to reduce the number of Asn-Gly sequences present in the parent enzyme in order to obtain mutated enzymes exhibiting improved pH and heat stabilities, in the application emphasis is put on removing, mutating, or modifying the $^{109}$Asn and the $^{218}$Asn residues in subtilisin BPN'. No examples are provided for any deletions or for modifying the Gly-residues.

International patent publication No. WO 87/05050 (Genex) discloses random mutation and subsequent screening of a large number of mutants of subtilisin BPN' for improved properties. In the application mutations are described in positions $^{218}$Asn, $^{131}$Gly, $^{254}$Thr, $^{166}$Gly, $^{116}$Ala, $^{188}$Ser, $^{126}$Leu, and $^{53}$Ser.

In EP 251 446 (Genencor) it is described how homology considerations at both primary and tertiary structural levels may be applied to identify equivalent amino acid residues whether conserved or not. This information together with the inventors knowledge of the tertiary structure of subtilisin BPN' lead the inventors to select a number of positions susceptible to mutation with an expectation of obtaining mutants with altered properties. The positions so identified are: $^{124}$Met, $^{222}$Met, $^{104}$Tyr, $^{152}$Ala, $^{156}$Glu, $^{166}$Gly, $^{169}$Gly, $^{189}$Phe, $^{217}$Tyr. Also $^{155}$Asn, $^{21}$Tyr, $^{22}$Thr, $^{24}$Ser, $^{32}$Asp, $^{33}$Ser, $^{36}$Asp, $^{46}$Gly, $^{48}$Ala, $^{49}$Ser, $^{50}$Met, $^{77}$Asn, $^{87}$Ser, $^{94}$Lys, $^{95}$Val, $^{96}$Leu, $^{107}$Ile, $^{110}$Gly, $^{170}$Lys, $^{171}$Tyr, $^{172}$Pro, $^{197}$Asp, $^{199}$Met, $^{204}$Ser, $^{213}$Lys, and $^{221}$Ser, which positions are identified as being expected to influence various properties of the enzyme. Also, a number of mutations are exemplified to support these suggestions. In addition to single mutations in these positions the inventors also performed a number of multiple mutations. Further the inventors identify $^{215}$Gly, $^{67}$His, $^{126}$Leu, $^{135}$Leu, and amino acid residues within the segments 97–103, 126–129, 213–215, and 152–172 as having interest, but mutations in any of these positions are not exemplified.

Especially of interest for the purpose of the present invention the inventors of EP 251 446 suggest to substitute $^{170}$Lys (in subtilisin BPN', type I-S1), specifically they suggest to introduce Glu or Arg for the original Lys. It appears that the Glu variant was produced and it was found that it was highly susceptible to autolytic degradation (cf. pages 48, 121, 123 (Table XXI includes an obvious error, but indicates a reduction in autolysis half-time from 86 to 13 minutes) and FIG. 32).

EP 260 105 (Genencor) describes modification of certain properties in enzymes containing a catalytic triad by selecting an amino acid residue within about 15 Å from the catalytic triad and replace the selected amino acid residue with another residue. Enzymes of the subtilase type described in the present specification are specifically mentioned as belonging to the class of enzymes containing a catalytic triad. In subtilisins positions 222 and 217 are indicated as preferred positions for replacement.

Also, it has been shown by Thomas, Russell, and Fersht (1985) *Nature* 318 375–376 that exchange of $^{99}$Asp into $^{99}$Ser in subtilisin BPN' changes the pH dependency of the enzyme.

In a subsequent article (1987) *J. Mol. Biol.* 193 803–813, the same authors also discuss the substitution of $^{156}$Ser in place of $^{156}$Glu.

Both these mutations are within a distance of about 15 Å from the active $^{64}$His.

In *Nature* 328 496–500 (1987) Russel and Fersht discuss the results of their experiments and present rules for changing pH-activity profiles by mutating an enzyme to obtain changes in surface charge.

WO 88/08028 (Genex) and WO 88/08033 (Amgen) both relate to modifications of amino acid residues in the calcium binding sites of subtilisin BPN'. The enzyme is said to be stabilized by substituting more negatively charged residues for the original ones.

In WO 89/06279 (Novo Nordisk A/S) position 170 is indicated as interesting and it is suggested to replace the existing residue with Tyr. However, no data are given in respect of such a variant. In WO 91/00345 (Novo Nordisk A/S) the same suggestion is made, and it is shown that the Tyr variant of position 170 in subtilisin 309 (type I-S2) exhibits an improved wash performance in detergents at a pH of about 8 (variant S003 in Tables III, IV, V, VI, VIII, X). The same substitution in combination with other substitutions in other positions also indicates an improved wash performance(S004, S011–S014, S022–S024, S019, S020, S203, S225, S227 in the same Table and Table VII) all in accordance with the generic concept of said application.

In EP 525 610 (Solvay) it is suggested to improve the stability of the enzyme (a type I-S2 subtilase closely related to subtilisin PB92) towards ionic tensides by decreasing the hydrophobicity in certain surface regions thereof. It is consequently suggested to substitute Gln for the Arg in position 164 (170 if using BPN' numbering). No variants comprising this substitution are disclosed in the application.

In WO 94/02618 (Gist-Brocades N.V.) a number of position 164 (170 if using BPN' numbering) variants of the I-S2 type subtilisin PB92 are described. Examples are provided showing substitution of Met, Val, Tyr, Ile, for the original Arg. Wash performance testing in powder detergents of the variants indicates a slight improvement. Especially for the Ile variant wash performance tests on cacao an improvement of about 20–30% is indicated. No stability data are provided.

In WO 95/30011, WO 95/30010, and WO 95/29979 (Procter & Gamble Company) describe 6 regions, especially position 199–220 (BPN' numbering), in both Subtilisin BPN' and subtilisin 309, which are designed to change (i.e. decrease) the adsorption of the enzyme to surface-bound soils. It is suggested that decreased adsorption by an enzyme to a substrate results in better detergent cleaning performance. No specific detergent wash performance data are provided for the suggested variants.

WO 95/27049 (Solvay S.A.) describes a subtilisin 309 type protease with following mutations: N43R+N116R+N117R (BPN' numbering). Data indicate the corresponding variant is having improved stability, compared to wildtype.

INDUSTRIAL APPLICATIONS OF SUBTILASES

Proteases such as subtilisins have found much utility in industry, particularly in detergent formulations, as they are useful for removing proteinaceous stains.

At present at least the following proteases are known to be commercially available and many of them are marketed in large quantities in many countries of the world.

Subtilisin BPN' or Novo, available from e.g. Sigma, St. Louis, U.S.A.

Subtilisin Carlsberg, marketed by Novo Nordisk A/S (Denmark) as ALCALASE® and by Gist-Brocades N.V. (Holland) as MAXATASE®;

Both of these belong to subtilase subgroup I-S1

Among the subtilase sub-group I-S2 the following are known to be marketed.

A *Bacillus lentus* subtilisin, subtilisin 309, marketed by Novo Nordisk A/S (Denmark) as SAVINASE®. A protein engineered variant of this enzyme is marketed as DURAZYM®.

Enzymes closely resembling SAVINASE®, such as subtilisin PB92, MAXACAL® marketed by Gist-Brocades N.V. (a protein engineered variant of this enzyme is marketed as MAXAPE®), OPTICLEAN® marketed by Solvay et Cie. and PURAFECT® marketed by Genencor International.

A *Bacillus lentus* subtilisin, subtilisin 147, marketed by Novo Nordisk A/S (Denmark) as ESPERASE®;

To be effective, however, such enzymes must not only exhibit activity under washing conditions, but must also be compatible with other detergent components during detergent production and storage.

For example, subtilisins may be used in combination with other enzymes active against other substrates, and the selected subtilisin should possess stability towards such enzymes, and also the selected subtilisin preferably should not catalyse degradation of the other enzymes. Also, the chosen subtilisin should be resistant to the action from other components in the detergent formulation, such as bleaching agents, oxidizing agents, etc., in particular an enzyme to be used in a detergent formulation should be stable with respect to the oxidizing power, calcium binding properties, and pH conditions rendered by the non-enzymatic components in the detergent during storage and in the wash liquor during wash.

The ability of an enzyme to catalyze the degradation of various naturally occurring substrates present on the objects to be cleaned during e.g. wash is often referred to as its washing ability, washability, detergency, or wash performance. Throughout this application the term wash performance will be used to encompass this property.

The ability of an enzyme to remain active in the presence of other components of a detergent composition prior to being put to use (normally by adding water in the washing process) is usually referred to as storage stability or shelf life. It is often measured as half-life, $t_{1/2}$. We will use the expression storage stability for this property throughout this application to encompass this property.

Naturally occurring subtilisins have been found to possess properties which are highly variable in relation to their washing power or ability under variations in parameters such as pH. Several of the above marketed detergent proteases, indeed, have a better performance than those marketed about 20 years ago, but for optimal performance each enzyme has its own specific conditions regarding formulation and wash conditions, e.g. pH, temperature, ionic strength (=I), active system (tensides, surfactants, bleaching agent, etc.), builders, etc.

As a consequence it is found that an enzyme possessing desirable properties at low pH and low I may be less attractive at more alkaline conditions and high I, or an enzyme exhibiting fine properties at high pH and high I may be less attractive at low pH, low I conditions.

Also, it has been found that the storage stability differs between the enzymes, but it has further been found that a specific enzyme exhibits large variations in storage stability in respect of different detergent formulations, dependent upon a number of parameters, such as pH, pI, bleach system, tensides, etc., and upon the physical state of the detergent compositions, which may be in powder, dust, or liquid form. Furthermore it may be concentrated or dilute.

The advent and development of recombinant DNA techniques has had a profound influence in the field of protein chemistry.

Through the application of this technology it is possible now to construct enzymes having desired amino acid sequences, and as indicated above a fair amount of research has been devoted to designing subtilisins with altered properties.

Among the proposals the technique of producing and screening a large number of mutated enzymes as described in EP 130 756 (Genentech) (U.S. Reissue Pat. No. 34,606 (Genencor)) and International patent publ. no. WO 87/05050 (Genex) correspond to a large extend to the classical method of isolating native enzymes, submit them to classical mutagenesis programs (using radiation or chemical mutagens) and screen them for their properties. The difference lies in that these methods are more efficient through the knowledge of the presence of a large number of variant enzymes substituted in a specific position.

A subtilisin enzyme typically comprises about 275 amino acid residues. Each residue is capable of being 1 out of 20 possible naturally occurring amino acids.

Therefore one very serious draw-back in that procedure is the very large number of mutations generated that have to be submitted to a number of preliminary screenings to determine their properties.

A procedure as outlined in these patent applications will consequently only be slightly better than the traditional random mutation procedures which have been known for years.

The other known techniques relate to changing specific properties, such as oxidation stability, thermal stability, Ca-stability, transesterification and hydrolysis rate (EP 260 105 (Genencor)), pH-activity profile (Thomas, Russell, and Fersht, supra), and substrate specificity (International patent publ. no. WO 88/07578 (Genentech)). None of these publications relates to changing either the wash performance of enzymes or their storage stability.

In International Patent Application no. PCT/DK 88/00002 (Novo Nordisk A/S) it is proposed to use the concept of homology comparison to determine which amino acid positions should be selected for mutation and which amino acids should be substituted in these positions in order to obtain a desired change in wash performance.

By using such a procedure the task of screening is reduced drastically, since the number of mutants generated is much smaller, but with that procedure it is only foreseen that enzymes exhibiting the combined useful properties of the parent enzyme and the enzyme used in the comparison may be obtained.

Thus, as indicated above no relationship has yet been identified between well defined properties of an enzyme such as those mentioned above and the wash performance and storage stability of an enzyme in various detergent compositions.

The problem seems to be that although much research has been directed at revealing the mechanism of enzyme activity, still only little is known about the factors in structure and amino acid residue combination that determine the properties, such as storage stability in detergents, of enzymes in relation to most of their characteristics, especially when the enzymes are present in complex mixtures.

Consequently there still exists a need for further improvement and tailoring of enzymes to detergent systems, as well as a better understanding of the mechanism of protease action and degradation in the practical use of cleaning or detergent compositions. Such an understanding could result in rules which may be applied for selecting mutations that with a reasonable degree of certainty will result in an enzyme exhibiting improved storage stability under specified conditions in a detergent composition.

SUMMARY OF THE INVENTION

It has now surprisingly been found that a subtilase variant having improved storage stability and/or improved performance in detergents, can be obtained by substituting one or more amino acid residues situated in, or in the vicinity of a hydrophobic domain of the parent subtilase for an amino acid residue more hydrophobic than the original residue, said hydrophobic domain comprising the residues corresponding to residues P129, P131, I165, Y167, Y171 of BLS309 (in BASBPN numbering), and said residues in the vicinity thereof comprises residues corresponding to the residues E136, G159, S164, R170, A194, and G195 of BLS309 (in BASBPN numbering), with the exception of the R170M, R170I and R170V variants of BABP92.

The present invention relates consequently in its first aspect to enzyme variants exhibiting improved stability and/or improved wash performance in detergent.

In its second aspect the invention relates to DNA constructs capable of expressing the enzymes of the first aspect, when inserted in a suitable manner into a host cell that subsequently is brought to express the subtilisin enzyme(s) of the first aspect.

In a third aspect the invention relates to the production of the subtilisin enzymes of the invention by inserting a DNA construct according to the second aspect into a suitable host, cultivating the host to express the desired subtilase enzyme, and recovering the enzyme product.

The invention relates, in part, but is not limited to, mutants of the genes expressing the subtilase sub-group I-S2 enzymes and the ensuing enzyme variants, as indicated above.

Other subtilase gene variants encompassed by the invention are such as those of the subtilase subgroup I-S1, e.g. Subtilisin BPN', and Subtilisin Carlsberg genes and ensuing variant Subtilisin BPN', Proteinase K, and Subtilisin Carlsberg enzymes, which exhibit improved stability in concentrated liquid detergents.

Still further subtilase gene variants encompassed by the invention are such as Proteinase K and other genes and ensuing variant Proteinase K, and other subtilase enzymes, which exhibit improved stability in concentrated liquid detergents.

Other examples of parent subtilase enzymes that can be modified in accordance with the invention are listed in Table I.

Further the invention relates to the use of the mutant enzymes in cleaning compositions and cleaning compositions comprising the mutant enzymes, especially detergent compositions comprising the mutant subtilisin enzymes. Specifically the invention relates to concentrated liquid detergent compositions comprising such enzyme variants.

ABBREVIATIONS

AMINO ACIDS

| | | |
|---|---|---|
| A = | Ala = | Alanine |
| V = | Val = | Valine |
| L = | Leu = | Leucine |
| I = | Ile = | Isoleucine |
| P = | Pro = | Proline |
| F = | Phe = | Phenylalanine |
| W = | Trp = | Tryptophan |
| M = | Met = | Methionine |
| G = | Gly = | Glycine |
| S = | Ser = | Serine |
| T = | Thr = | Threonine |
| C = | Cys = | Cysteine |
| Y = | Tyr = | Tyrosine |
| N = | Asn = | Asparagine |
| Q = | Gln = | Glutamine |
| D = | Asp = | Aspartic Acid |
| E = | Glu = | Glutamic Acid |
| K = | Lys = | Lysine |

-continued

| | | |
|---|---|---|
| R = | Arg = | Arginine |
| H = | His = | Histidine |
| X = | Xaa = | Any amino acid |

NUCLEIC ACID BASES

| | |
|---|---|
| A = | Adenine |
| G = | Guanine |
| C = | Cytosine |
| T = | Thymine (only in DNA) |
| U = | Uracil (only in RNA) |

VARIANTS

In describing the various enzyme variants produced or contemplated according to the invention, the following nomenclatures have been adapted for ease of reference:

Original amino acid(s) position(s) substituted amino acid (s)

According to this the substitution of Glutamic acid for glycine in position 195 is designated as:

Gly 195 Glu or G195E a deletion of glycine in the same position is:

Gly 195* or G195* and insertion of an additional amino acid residue such as lysine is:

Gly 195 GlyLys or G195GK

Where a deletion in comparison with the sequence used for the numbering is indicated, an insertion in such a position is indicated as:

*36 Asp or *36D for insertion of an aspartic acid in position 36

Multiple mutations are separated by pluses, i.e.:

Arg 170 Tyr+Gly 195 Glu or R170Y+G195E representing mutations in positions 170 and 195 substituting tyrosine and glutamic acid for arginine and glycine, respectively.

POSITIONS

In describing the variants in this application and in the appended claims use is made of the alignment of various subtilases in Siezen et al., Supra. In other publications relating to subtilases other alignments or the numbering of specific enzymes have been used. It is a routine matter for the skilled person to establish the position of a specific residue in the numbering used here. Reference is also made to FIG. 1 showing an alignment of residues relevant for the present invention from a large number of subtilases. Reference is also made to Table I of WO 91/00345 showing an alignment of residues relevant for the present invention from a number of subtilases.

TABLE I

Presently established Subtilases (from Siezen et al, supra)

| Organism | cDNA, gene | enzyme | acronym |
|---|---|---|---|
| PROKARYOTES | | | |
| Bacteria: Gram-positive | | | |
| Bacillus subtilis 168 | aprA | subtilisin I168, apr | ABSS168 |
| Bacillus amyloliquefaciens | apr | subtilisin BPN' (NOVO) | BASBPN |
| Bacillus subtilis DY | – | subtilisin DY | BSSDY |

TABLE I-continued

Presently established Subtilases (from Siezen et al, supra)

| Organism | cDNA, gene | enzyme | acronym |
|---|---|---|---|
| Bacillus licheniformis | + | subtilisin Carlsberg | BLSCAR |
| Bacillus lentus | + | subtilisin 147 | BLS147 |
| Bacillus alcalophilus PB92 | + | subtilisin PB92 | BAPB92 |
| Bacillus sp. DSM 4828 | – | alkaline protease | BDSM48 |
| Bacillus YaB | ale | alkaline elastase YaB | BYSYAB |
| Bacillus subtilis 168 | epr | min. extracell. prot. | BSEPR |
| Bacillus subtilis | bpf | bacillopeptidase F | BSBPF |
| Bacillus subtilis IFO3013 | ispI | intracell.ser. prot.1 | BSISP1 |
| Bacillus subtilis A50 | – | intracell.ser. prot. | BSIA50 |
| Bacillus thuringiensis | – | extracell. ser. prot. | BTFINI |
| Bacillus cereus | – | extracell. ser. prot. | BCESPR |
| Nocardiopsis dassonvillei | – | alkaline ser. prot. | NDAPII |
| Thermoactinomyces vulgaris | – | thermitase | TVTHER |
| Enterococcus faecalis | cylA | cytolysin component A | EFCYLA |
| Staphylococcus epidermidis | epiP | epidermin lead. prot. | SEEPIP |
| Streptococcus pyogenes | scpA | C5a peptidase | SPSCPA |
| Lactococcus lactis SK11 | prtP | SK11 cell wall prot. | LLSK11 |
| Bacteria: Gram-negative | | | |
| Dichelobacter nodosus | + | basic protease | DNEBPR |
| Xanthomonas campestris | + | extracellular prot. | XCEXPR |
| Serratia marcescens | + | extracell. ser. prot. | SMEXSP |
| Thermus aquaticus YT-1 | pstI | aqualysin I | TAAQUA |
| Thermus rT41A | + | T41A protease | TRT41A |
| Vibrio alginolyticus | proA | protease A | VAPROA |
| Streptomyces rutgersensis | – | proteinase D | SRESPD |
| Archaea | | | |
| halophilic strain 172P1 | – | halophil extra. prot. | ARB172 |
| Cyanobacteria | | | |
| Anabaena variabilis | prcA | Ca-dependent protease | AVPRCA |
| LOWER EUKARYOTES | | | |
| Fungi | | | |
| Tritirachium album Limber | + | proteinase K | TAPROK |
| Tritirachium album | + | proteinase R | TAPROR |
| Tritirachium album | proT | proteinase T | TAPROT |
| Aspergillus oryzae | + | alkaline protease | AOALPR |
| Malbranchea pulchella | – | thermomycolin | MPTHMY |
| Acremonium chrysogenum | alp | alkaline protease | ACALPR |
| Yeasts | | | |
| Kluyveromyces lactis | kex1 | Kex1 ser. proteinase | KLKEX1 |
| Saccharomyces cerevisiae | kex2 | Kex2 ser. proteinase | SCKEX2 |
| Saccharomyces cerevisiae | prb1 | protease B | SCPRB1 |
| Yarrowia lipolytica | xpr2 | alk. extracell. prot. | YLXPR2 |
| HIGHER EUKARYOTES | | | |
| Worms | | | |
| Caenorhabditis elegans | bli4 | cuticle protease | CEBLI4 |
| Insects | | | |
| Drosophila (fruit fly) | fur1 | furin 1 | DMFUR1 |
| Drosophila (fruit fly) | fur2 | furin 2 | DMFUR2 |
| Plants | | | |
| Cucumis melo (melon) | – | cucumisin | CMCUCU |
| Mammals | | | |
| Human (also rat, mouse) | fur | furin | HSFURI |
| Human (also mouse) | + | insulinoma PC2 prot. | HSIPC2 |
| Mouse | + | pituitary PC3 prot. | MMPPC3 |
| Human | + | tripeptidyl peptid.II | HSTPP |

References Used for Table I

References to amino acid sequences (GenBank®/EMBL Data Bank accession numbers are shown in brackets):

ARB172 Kamekura and Seno, (1990) Biochem. Cell Biol. 68 352–359 (amino acid sequencing of mature protease residues 1–35; residue 14 not determined).

BSS168 Stahl and Ferrari, (1984) J. Bacteriol. 158, 411–418 (K01988). Yoshimoto, Oyama et al. (1488) J. Biochem. 103, 1060–1065 (the mature subtilisin from B. subtilis var. amylosacchariticus differs in having T130S and T162S). Svendsen, et al. (1986) FEBS Lett. 196, 228–232 (PIR A23624; amino acid sequencing; the mature alkaline mesentericopeptidase From B. mesentericus differs in having S85A, A88S, S89A, S183A and N259S).

BASBPN Wells, et al. (1983) Nucl. Acids Res. 11 7911–7925 (X00165). Vasantha et al., (1984) J. Bacteriol. 159 811–814(K02496).

BSSDY Nedkov et al. (1983) Hoppe-Seyler's Z. Physiol. Chem. 364 1537–1540 (PIR A00969; amino acid sequencing).

BLSCAR Jacobs et al. (1985) Nucleic Acids Res. 13 8913–8926 (X03341). Smith et al. (1968) J. Biol. Chem. 243 2184–2191 (PIR A00968; amino acid sequencing; mature protease sequence differs in having T103S, P129A, S158N, N161S and S212N).

BLS147 Hastrup et al. (1989) PCT Patent Appl. WO 8906279. Pub. Jul. 13 1989. (Esperase® from B. lentus). Takami et al. (1990) Appl. Microbiol. Biotechnol., 33 519–523 (amino acid sequencing of mature alkaline protease residues 1–20 from Bacillus sp. no. AH-101; this sequence differs from BLS147 in having N11S).

BABP92 van der Laan et al. (1991) Appl. Environ. Microbiol. 57 901–909. (Maxacal®). Hastrup et al. (1989) PCT Patent Appl. WO 8906279. Pub. Jul. 13, 1989. (subtilisin 309). Savinase®, from B. lentus differs only in having N87S). Godette et al. (1991) Abstracts 5th Protein Society Symposium, June 6, Baltimore: abstract M8 (a high-alkaline protease from B. lentus differs in having N87S, S99D, S101R, S103A, V104I and G159S).

BDSM48 Rettenmaier et al. (1990) PCT Patent Appl. WO 90/04022. Publ. Apr. 19, 1990.

BYSYAB Kaneko et al. (1989) J. Bacteriol. 171 5232–5236 (M28537).

BSEPR Sloma et al. (1988) J. Bacteriol. 170 5557–5563 (M22407). Bruckner (1990) Mol. Gen. Genet. 221 486–490 (X53307).

BSBPF Sloma et al. (1990) J. Bacteriol. 172 1470–1477 (M29035; corrected). Wu et al. (1990) J. Biol Chem. 265 6845–6850 (J05400; this sequence differs in having A169V and 586 less C-terminal residues due to a frameshift).

BSISP1 Koide et al. (1986) J. Bacteriol. 167 110–116 (M13760).

BSIA50 Strongin et al. (1978) J. Bacteriol. 133 1401–1411 (amino acid sequencing of mature protease residues 1–54; residues 3, 39, 40, 45, 46, 49 and 50 not determined).

BTFINI Chestukhina et al. (1985) Biokhimiya 50 1724–1730 (amino acid sequencing of mature protease residues 1–14 from B. thuringiensis variety israeliensis, and residues 1–16 and 223–243 from variety finitimus). Kunitate et al. (1989) Agric. Biol. Chem. 53 3251–3256 (amino acid sequencing of mature protease residues 6–20 from variety kurstaki. BTKURS).

BCESPR Chestukhina et al. (1985) Biokhimiya 50 1724–1730 (amino acid sequencing of mature residues 1–16 and 223–243).

NDAPII Tsujibo et al. (1990) Agric. Biol. Chem. 54 2177–2179 (amino acid sequencing of mature residues 1–26).

TVTHER Meloun et al. (1985) FEBS Lett. 183 195–200 (PIR A00973; amino acid sequencing of mature protease residues 1–274).

EFCYLA Segarra et al. (1991) Infect. Immun. 59 1239–1246.

SEEPIP Schnell et al. (1991) personal communication (Siezen et al. (supra)).

SPSCPA Chen et al. (1990) J. Biol. Chem. 265 3161–3167 (J05224).

DNEBPR Kortt et al. (1991) Abstracts 5th Protein Society Symposium, June 22–26, Baltimore, abstract S76.

LLSK11 Vos et al. (1989) J. Biol. Chem. 264 13579–13585 (J04962). Kok et al. (1988) Appl. Environ. Microbiol. 54 231–238 (M24767; the sequence from strain Wg2 differs in 44 positions, including 18 differences in the protease domain, and a deletion of residues 1617–1676). Kiwaki et al. (1989) Mol. Microbiol. 3 359–369 (X14130; the sequence from strain NCD0763 differs in 46 positions, including 22 in the protease domain, and a deletion of residues 1617–1676).

XCEXPR Liu et al. (1990) Mol. Gen. Genet. 220 433–440.

SMEXSP Yanagida et al. (1986) J. Bacteriol. 166 937–994 (M13469).

TAAQUA Terada et al. (1990) J. Biol. Chem. 265 6576–6581 (J054I4).

TRT41A McHale et al. (1990) Abstracts 5th Eur. Congr. Biotechn. Christiansen, Munck and Villadsen (eds), Munksgaard Int. Publishers, Copenhagen.

VAPROA Deane et al. (1989) Gene 76 281–288 (M25499).

SRESPD Lavrenova et al. (1984) Biochemistry USSR. 49 447–454 (amino acid sequencing of residues 1–23; residues 13, 18 and 19 not determined).

AVPRCA Maldener et al. (1991) Mol. Gen. Genet. 225 113–120 (the published sequence has 28 uncertain residues near position 200–210 due to a frameshift reading error).

TAPROK Gunkel and Gassen (1989) Eur. J. Biochem. 179 185–194 (X14688/XI4689). Jany et al. (1986) J. Biol. Chem. Hoppe-Seyler 367 87(PIR A24541; amino acid sequencing; mature protease differs in having S745G, SILST204-208DSL and VNLL264-267FNL).

TAPROR Samal et al. (1990) Mol. Microbiol. 4 1789–1792 (X56116).

TAPROT Samal et al. (1989) Gene 85 329–333.

AOALPR Tatsumi et al. (1989) Mol. Gen. Genet. 219 33–38. Cheevadhanarah et al. (1991) EMBL Data Library (X54726).

MPTHMY Gaucher and Stevenson (1976) Methods Enzymol. 45 415–433 (amino acid sequencing of residues 1–28, and hexapeptide LSGTSM with active site serine).

ACALPR Isogai et al. (1991) Agric. Biol. Chem. 55 471–477. Stepanov et al. (1986) Int. J. Biochem. 18 369–375 (amino acid sequencing of residues 1–27: the mature protease differs in having H13[1]Q, R13[2]N and S13[6]A).

KLKEX1 Tanguy-Rougeau, Wesolowski-Louvel and Fukuhara (1988) FEBS lett. 234 464–470 (X07038).

SCKEX2 Mizuno et al. (1988) Biochem. Biophys. Res. Commun. 156 246–254(M24201).

SCPRB1 Moehle et al. (1987) Mol. Cell. Biol. 7 4390–4399 (M18097).

YLXYPR2 Davidow et al. (1987) J. Bacteriol. 169 4621–4629 (M17741). Matoba et al. (1988) Mol. Cell Biol. 8 4904–4916 (M23353).

CEBL14 Peters and Rose (1991) The Worm Breeder's Gazette 11 28.

DMFUR1 Roebroek et al. (1991) FEBS Lett. 289 133–137 (X59384).

DMFUR2 Roebroek et al. (1992) 267 17208–17215.
CMCUCU Kaneda et al. (1984) *J. Biochem.* 95 825–829 (amino acid sequencing of octapeptide NIISGTSM with active site serine).
HSFURI van den Ouweland et al. (1990) *Nucl. Acids Res.* 18 664 (X04329) (the sequence of mouse furin differs in 51 positions, including five in the catalytic domain: A15E, Y21F, S223F, A232V and N258[2]D). Misumi et al. (1990) *Nucl. Acids Res.* 18 6719 (X55660: the sequence of rat furin differs in 49 positions, including three in the catalytic domain: A15E, Y21F, H24R).
HSIPC2 Smeekens and Steiner (1990) *J. Biol. Chem.* 265 2997–3000 (J05252). Seidah et al. (1990) *DNA Cell Biol.* 9 415–424 (the sequence of mouse pituitary PC2 protease differs in 23 positions, including seven in the protease domain: I4F, S42[2]Y, E45D, N76S, D133E, V134L and G239[1]D).
MMPPC3 Smeekens et al. (1991) *Proc. Natl. Acad. Sci. USA* 88 340–344 (M58507). Seidah et al. (1990) *DNA Cell Biol.* 9 415–424 (M55668/M55669; partial sequence).
HSTPP Tomkinson and Jonsson (1991) *Biochemistry* 30 168–174 (J05299).

BRIEF DESCRIPTION OF THE FIGURES

FIG. 1 shows an alignment of a number of the subtilases mentioned in Table I;

DETAILED DESCRIPTION OF THE INVENTION

Figure 2:
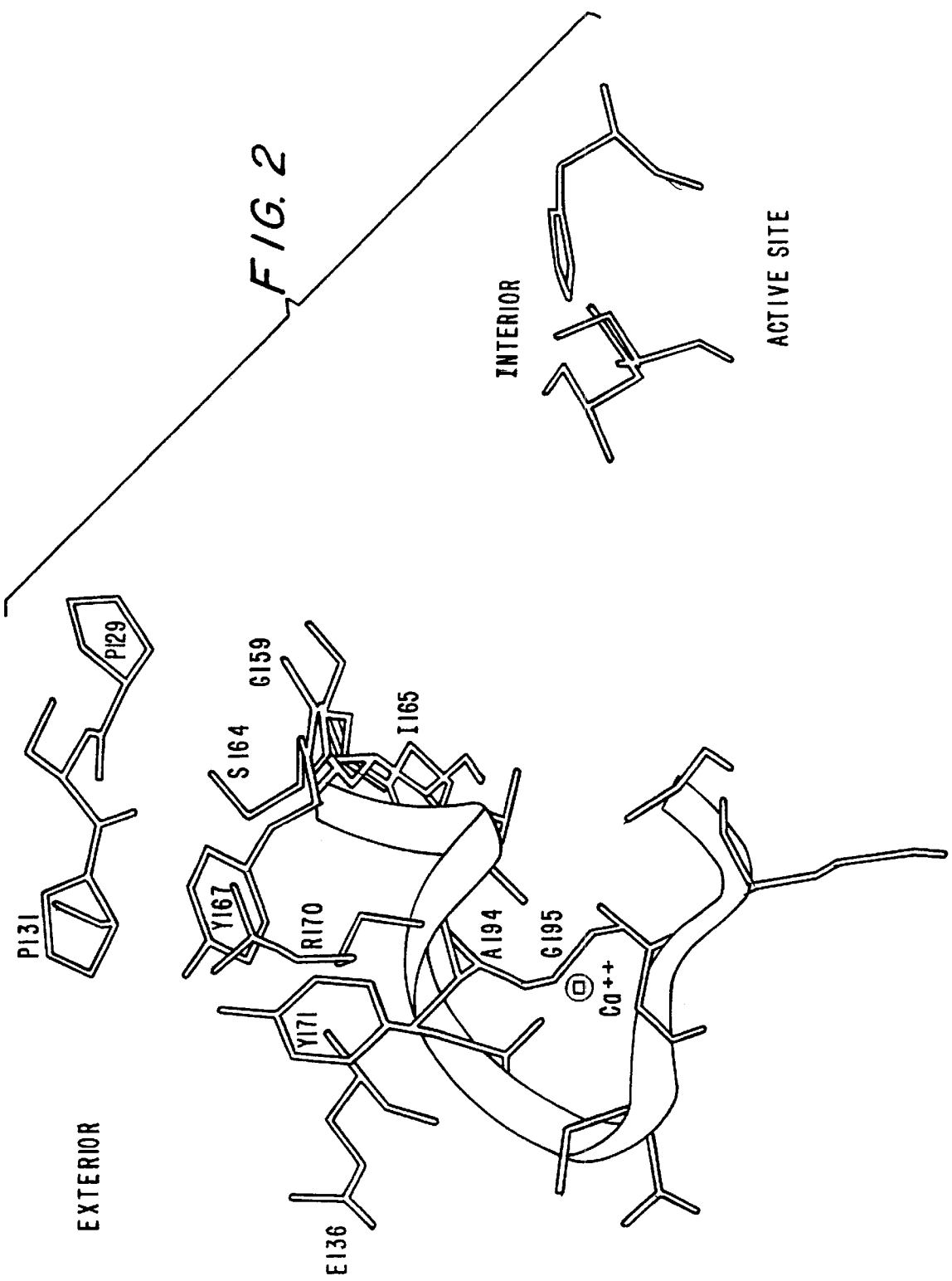
FIG. 2 is a 3-dimensional representation of subtilisin 309 showing the location of the hydrophobic domain and some of the amino acid residues in the vicinity thereof to be substituted according to the invention.

It has surprisingly been found that the storage stability and/or improved performance in detergents of subtilases generally is improved when amino acid residues situated in, or in the vicinity of a hydrophobic domain comprising the residues P129, P131, I165, Y167, Y171 of subtilisin 309 are substituted for a more hydrophobic residue. The residues in question are especially E136, G159, S164, R170, A194, and G195.

Further, said variant exhibits a particularly high improved stability in liquid detergents and in detergents in a shaped solid form.

FIG. 2 shows the hydrophobic domain in subtilisin 309 and residues in the vicinity thereof a number of which are to be substituted in order to increase the hydrophobicity of the domain. This may be achieved by substituting hydrophobic residues for non-hydrophobic residues and/or by substituting residues to become even more hydrophobic than in the parent enzyme.

The same principle applies to the corresponding domain in other subtilases, the identification of which is within the skills of the average person working in this technical field. Graphic representations like the one in FIG. 2 can be produced for other subtilases to determine the target residues to be substituted according to the invention.

A number hereof is indicated in Table II below:

TABLE II residues in hydrophobic domain and the vicinity thereof

| Pos\Enz. | BASBPN | BLSCAR | BLS309 | BLS147 | TVTHER |
|---|---|---|---|---|---|
| domain | | | | | |
| 129 | P | A | P | T | T |
| 131 | G | G | P | G | G |
| 165 | V | I | I | V | P |
| 167 | Y | Y | Y | Y | Y |
| 171 | Y | Y | Y | Y | Y |
| Vicinity | | | | | |
| 136 | K | K | E | E | Q |
| 159 | S | S | G | G | T |
| 164 | T | T | S | G | A |
| 170 | K | K | R | R | Y |
| 194 | P | A | A | P | S |
| 195 | E | E | G | E | V |

Table II was constructed using the alignment shown in FIG. 2. It is obvious that similar or larger tables covering other subtilases may easily be produced by the skilled person.

Consequently the invention relates to subtilase variants in which the amino acid sequence has been changed through mutating the gene of the subtilisin enzyme, which it is desired to modify (the parent enzyme or gene), in the codon responsible for the expression of the amino acid residue in positions 129, 131, 165, 167, 171, 136, 159, 164, 170, 194, and 195, which residues are more hydrophobic than the residue(s) in the parent enzyme, especially such hydrophobic residues that comprise a relatively long hydrophobic side chain, such as Ile, Leu, and Val, whereby, when the mutated gene is expressed, the amino acid residue is substituted by a more hydrophobic residue, which increases the hydrophobicity of the domain as such.

Hydrophobic amino acid residues are generally the following: Val (V), Ile (I), Leu (L), Met (M), Phe (F), Pro (P) and Trp(W). Among these Val, Ile and Leu are preferred.

By looking at Table II and applying the principle of the invention a number of candidates for substitution becomes clear.

For both BASBPN and BLSCAR it seems appropriate to make substitutions in positions 129, 131, 136, 159, 164, 167, 170, 171 and 195. In BLS309 positions 136, 164, 167, and 170, 171 would be the first choices, and positions 159 and 195 also would be a second choice. In BLS147 positions 129, 131, 136, 167, 170, 171 and 195 are the first choice, while positions 159 and 164 are second. Finally, in TVTHER positions 129, 131, 136, 167, 171 and 194 are the first choices, with 164 as a second one.

According to the invention it would entail an advantage to substitute the Gly residues in the hydrophobic domain to bulkier and more hydrophobic residues.

Such considerations apply for any hydrophilic or hydrophobic residue that may occupy any of the above mentioned position, meaning that any increase in hydrophobicity seems to be advantageous. This means that e.g. a very hydrophilic residue such as the charged residues Arg (R), Asp (D), Glu (E) or Lys (K) may be substituted by any residue that is less hydrophilic. Such less hydrophilic residues comprises the residues Gly (G), Cys (C), Ser (S), Ala (A), Thr (T), Tyr (Y), Gln (Q), His (H) or Asn (N). It also means that a Tyr(Y) may be substituted by a more hydrophobic residue such as Phe(F), Leu(L), or Ile(I).

Similar considerations can be applied to other subtilases having a hydrophobic domain in this part of the surface of the enzyme.

In the context of this invention a subtilase is defined in accordance with Siezen et al. supra. In a more narrow sense, applicable to many embodiments of the invention, the subtilases of interest are those belonging to the subgroups I-S1 and I-S2. In a more specific sense, many of the embodiments of the invention relate to serine proteases of gram-positive bacteria which can be brought into substantially unambiguous homology in their primary structure, with the subtilases listed in Table I above.

The present invention also comprises any one or more substitutions in the above mentioned positions in combination with any other substitution, deletion or addition to the amino acid sequence of the parent enzyme. Especially combinations with other substitutions known to provide improved properties to the enzyme are envisaged.

Such combinations comprise the positions: 222 (improve oxidation stability), 218 (improves thermal stability), substitutions in the Ca-binding sites stabilising the enzyme, e.g. position 76, and many other apparent from the prior art.

Furthermore combinations with the variants mentioned in EP 405 901 are also contemplated specifically.

VARIANTS

A: Single Variants

Subtilisin BPN', Subtilisin Carlsberg, Subtilisin 168, and Subtilisin DY variants:

A129V, A129I, A129L, A129M, A129F,
G131V, G131I, G131L, G131M, G131F,
K136V, K136I, K136L, K136M, K136F,
S159V, S159I, S159L, S159M, S159F,
T164V, T164I, T164L, T164M, T164F,
Y167V, Y167I, Y167L, Y167M, Y167F,
K170V, K170I, K170L, K170M, K170F,
Y171V, Y171I, Y171L, Y171M, Y171F,
A194V, A194I, A194L, A194M, A194F,
E195V, E195I, E195L, E195M, E195F,

Thermitase variants:

A129V, A129I, A129L, A129M, A129F,
G131V, G131I, G131L, G131M, G131F,
Q136V, Q136I, Q136L, Q136M, Q136F,
T159V, T159I, T159L, T159M, T159F,
A164V, A164I, A164L, A164M, A164F,
Y167V, Y167I, Y167L, Y167M, Y167F,
Y171V, Y171I, Y171L, Y171M, Y171F,
Y170V, Y170I, Y170L, Y170M, Y170F,
S194V, S194I, S194L, S194M, S194F,

Subtilisin 309, Subtilisin 147, and Bacillus PB92 protease variants:

T129V, T129I, T129L, T129M, T129F,
G131V, G131I, G131L, G131M, G131F,
E136V, E136I, E136L, E136M, E136F,
G159V, G159I, G159L, G159M, G159F,
G164V, G164I, G164L, G164M, G164F, (BLS147)
S164V, S164I, S164L, S164M, S164F, (BLS309 AND BAPB92)
Y167A, Y167H, Y167N, Y167P, Y167C, Y167W, Y167Q, Y167S, Y167T,
Y167G, Y167V, Y167I, Y167L, Y167M, Y167F R170W, R170A, R170H, R170N, R170P, R170Q, R170S, R170T, R170Y (disclaimed for BLS309), R170V (disclaimed for BAPB92), R170I (disclaimed for BAPB92),
R170L, R170M (disclaimed for BAPB92), R170F, R170G, R170C,
Y171A, Y171H, Y171N, Y171P, Y171C, Y171W, Y171Q, Y171S, Y171T,
Y171G, Y171V, Y171I, Y171L, Y171M, Y171F,
A194V, A194I, A194L, A194M, A194F, (BLS309 AND BAPB92)
P194V, P194I, P194L, P194M, P194F, (BLS147)
E195V, E195I, E195L, E195M, E195F, (BLS147)
G195V, G195I, G195L, G195M, G195F, (BLS309 AND BAPB92

B: Combination Variants

Any of the above variants are contemplated to prove advantageous if combined with other variants in any of the positions:

27, 36, 57, 76, 97, 101, 104, 120, 123, 206, 218, 222, 224, 235 and 274.

Specifically the following BLS309 and BAPB92 variants are considered appropriate for combination: K27R, *36D, S57P, N76D, G97N, S101G, V104A, V104N, V104Y, H120D, N123S, A194P, Q206E, N218S, M222S, M222A, T224S, K235L and T274A.

Also such variants comprising any one or two of the substitutions X167V, X167M, X167F, X167L, X167I, X170V, X170M, X170F, X170L, and/or X170I in combination with any one or more of the other substitutions, deletions and/or insertions mentioned above are advantageous.

Furthermore variants comprising any of the variants V104N+S101G, K27R+V104Y+N123S+T274A, or N76D+V104A or other combinations of these mutations (V104N, S101G, K27R, V104Y, N123S, T274A, N76D, V104A), in combination with any one or more of the substitutions, deletions and/or insertions mentioned above are deemed to exhibit improved properties.

Specific combinations to be mentioned are:

a) S57P+R170L
a') S57P+R170I
b) R170L+N218S
b') R170I+N218S
c) S57P+R170L+N218S
c') S57P+R170I+N218S
c") S57P+V104Y+R170L+N218S
c''') S57P+V104Y+R170I+N218S
d) R170L+N218S+M222A
d') R170I+N218S+M222S
d") R170L+N218S+M222A
d''') R170I+N218S+M222S
e) S57P+R170L+S188P+A194P
e') S57P+R170I+S188P+A194P
f) Y167L+R170L
f') Y167L+R170I
g) Y167I+R170L
(g') Y167I+R170I
h) N76D+R170L+N218S
h') N76D+R170I+N218S
i) S57P+N76D+R170L+N218S
i') S57P+N76D+R170I+N218S
j) N76D+R170L+N218S+M222A j') N76D+R170I+N218S+M222S
j") N76D+R170L+N218S+M222A
j'") N76D+R170L+N218S+M222S
k) S57P+R170I+S 188P+A194P+N218S
k') S57P+R170I+S188P+A194P+N218S
l) *36D+N76D+H120D+R170L+G195E+K235L
l') *36D+N76D+H120D+R170I+G195E+K235L
l") *36D+N76D+H120D+Y167I+R170L+G195E+K235L
l'") *36D+N76D+H120D+Y167I+R170I+G195E+K235L
m) N76D+H120D+R170L+G195E+K235L
m') N76D+H120D+R170I+G195E+K235L
m") N76D+H120D+Y167I+R170L+G195E+K235L
m'") N76D+H120D+Y167I+R170I+G195E+K235L
n) *36D+G97N+V104Y+H120D+R170L+A194P+G195E+K235L
n') *36D+G97N+V104Y+H120D+R170I+AI94P+G195E+K235L
o) S57P+R170L+Q206E
o') S57P+R170I+Q206E
p) R170L+Q206E
p') R170I+Q206E
q) Y167I+R170L+Q206E
q') Y167I+R170I+Q206E
r) Y167F+R170L
r') Y167F+R170I
t) Y167I+R170L+A194P
t') Y167I+R170I+A194P
t") Y167L+R170L+A194P
t'") Y167L+R170I+A194P
u) Y167I+R170L+N218S
u') Y167I+R170I+N218S
u") Y167L+R170L+N218S
u'") Y167L+R170I+N218S
v) Y167I+R170L+A194P+N218S
v') Y167I+R170I+A194P+N218S
v") Y167L+R170L+A194P+N218S
v'") Y167L+R170I+A194P+N218S
x) R170L+P131V
x') R170I+P131V
y) *36D+Y167I+R170L
y') *36D+Y167I+R170I
z) Y167I+Y171I
aa) Y167V+R170L
aa') Y167V+R170I
bb) R170L+Y171I
bb') R170I+Y171L
bb") R170L+Y171L
bb'") R170I+Y171I
cc) Y167I+Y171L+N218S
cc') Y167I+Y171I+N218S

DETERGENT COMPOSITIONS COMPRISING THE MUTANT ENZYMES

The present invention also comprises the use of the mutant enzymes of the invention in cleaning and detergent compositions and such compositions comprising the mutant subtilisin enzymes. Such cleaning and detergent compositions can in principle have any physical form, but the subtilase variants are preferably incorporated in liquid detergent compositions or in detergent compositions in the form of bars, tablets, sticks and the like for direct application, wherein they exhibit improved enzyme stability or performance.

Among the liquid compositions of the present invention are aqueous liquid detergents having for example a homogeneous physical character, e.g. they can consist of a micellar solution of surfactants in a continuous aqueous phase, so-called isotropic liquids.

Alternatively, they can have a heterogeneous physical phase and they can be structured, for example they can consist of a dispersion of lamellar droplets in a continuous aqueous phase, for example comprising a deflocculating polymer having a hydrophilic backbone and at least one hydrophobic side chain, as described in EP-A-346 995 (Unilever) (incorporated herein by reference). These latter liquids are heterogeneous and may contain suspended solid particles such as particles of builder materials e.g. of the kinds mentioned below.

Concerning powder detergent compositions such compositions comprise in addition to any one or more of the subtilisin enzyme variants in accordance to any of the preceding aspects of the invention alone or in combination any of the usual components included in such compositions which are well-known to the person skilled in the art.

Such components comprise builders, such as phosphate or zeolite builders, surfactants, such as anionic, cationic, nonionic or zwitterionic type surfactants, polymers, such as acrylic or equivalent polymers, bleach systems, such as perborate- or amino-containing bleach precursors or activators, structurants, such as silicate structurants, alkali or acid to adjust pH, humectants, and/or neutral inorganic salts.

Furthermore, a number of other ingredients are normally present in the compositions of the invention, such as Cosurfactants, Tartrate Succinate Builder, Neutralization System, Suds Suppressor, Other Enzymes and Other Optional Components.

The weight ratio of anionic surfactant to nonionic surfactant is preferably from 1:1 to 5:1. The compositions have a pH in a 10% by weight solution in water at 20° C. of from 7.0 to 9.0, a Critical Micelle Concentration of less than or equal to 200 ppm, and an air/water Interfacial Tension at the Critical Micelle Concentration of less than or equal to 32 dynes/cm at 35° C. in distilled water. The compositions are preferably clear, homogeneous and phase stable, and have good cleaning performance and enzyme stability.

VARIOUS COMPONENTS

1. Anionic Surfactant

The compositions of the present invention contain from about 10% to about 50%, preferably from about 15% to about 50%, more preferably from about 20% to 40%, and most preferably from 20% to about 30%, by weight of a natural or synthetic anionic surfactant. Suitable natural or synthetic anionic surfactants are e.g. soaps and such as disclosed in U.S. Pat. Nos. 4,285,841 and 3,929,678.

Useful anionic surfactants include the water-soluble salts, particularly the alkali metal, ammonium and alkylolammonium (e.g., monoethanolammonium or triethanolammonium) salts, of organic sulfuric reaction products having in their molecular structure an alkyl group containing from about 10 to about 20 carbon atoms and a sulfonic acid or sulfuric acid ester group. (Included in the term "alkyl" is the alkyl portion of aryl groups.) Examples of this group of synthetic surfactants are the alkyl sulfates, especially those obtained by sulfating the higher alcohols ($C_8$–$C_{18}$ carbon atoms) such as those produced by reducing the glycerides of tallow or coconut oil; and the alkylbenzene sulfonates in which the alkyl group contains from about 9 to about 15 carbon atoms, in straight chain or branched chain configuration, e.g., those of the type described in U. S. Pat. Nos. 2,220,099 and 2,477,383. Especially valuable are linear straight chain alkylbenzene sulfonates in which the average number of carbon atoms in the alkyl group is from about 11 to 14.

Other anionic surfactants herein are the water-soluble salts of: paraffin sulfonates containing from 8 to about 24 (preferably about 12 to 18) carbon atoms; alkyl glyceryl ether sulfonates, especially those ethers of $C_8$–$C_{18}$ alcohols (e.g., those derived from tallow and coconut oil); alkyl phenol ethylene oxide ether sulfates containing from 1 to about 4 units of ethylene oxide per molecule and from 8 to 12 carbon atoms in the alkyl group; and alkyl ethylene oxide ether sulfates containing 1 to 4 units of ethylene oxide per molecule and from 10 to 20 carbon atoms in the alkyl group.

Other useful anionic surfactants include the water-soluble salts of esters of α-sulfonated fatty acids containing from 6 to 20 carbon atoms in the fatty acid group and from 1 to 10 carbon atoms in the ester group; water-soluble salts of 2-acyloxy-alkane-1-sulfonic acids containing from 2 to 9 carbon atoms in the acyl group and from 9 to 23 carbon atoms in the alkane moiety; water-soluble salts of olefin sulfonates containing from 12 to 24 carbon atoms; and β-alkyloxy alkane sulfonates containing from 1 to 3 carbon atoms in the alkyl group and from 8 to 20 carbon atoms in the alkane moiety.

Preferred anionic surfactants are soaps, the $C_{10}$–$C_{18}$ alkyl sulfates and alkyl ethoxy sulfates containing an average of up to 4 ethylene oxide units per mole of alkyl sulfate, $C_{11}$–$C_{13}$ linear alkyl benzene sulfonates, and mixtures thereof.

2. Nonionic Surfactant

Another optional ingredient is from 2% to 14% preferably from 2% to 8%, most preferably from 3% to 5% by weight, of an optionally ethoxylated nonionic surfactant. The weight ratio of natural or synthetic anionic surfactant (on an acid basis) to nonionic surfactant is from 1:1 to 5:1 preferably from 2:1 to 5:1, most preferably from 3:1 to 4:1. This is to ensure the formation and adsorption of sufficient hardness surfactants at the air/water interface to provide good greasy/oily soil removal.

The optionally ethoxylated nonionic surfactant is of the formula $R^1(OC_2H_4)_n$ OH, wherein $R^1$ is a $C_{10}$–$C_{16}$ alkyl group or a $C_8$–$C_{12}$ alkyl phenyl group, n is from 3 to 9, and said nonionic surfactant has an HLB (Hydrophilic-Lipophilic Balance) of from 6 to 14, preferably from 10 to 13. These surfactants are more fully described in U.S. Pat. Nos. 4,285,841, and 4,284,532, Particularly preferred are condensation products of $C_{12}$–$C_{15}$ alcohols with from 3 to 8 moles of ethylene oxide per mole of alcohol, e.g., $C_{12}$–$C_{13}$ alcohol condensed with about 6.5 moles of ethylene oxide per mole of alcohol. Other nonionic surfactants to be mentioned are APG, EGE, and glucamide surfactants.

3. Detergency Builder

Among the usual detergent ingredients which may be present in usual amounts in the detergent compositions of this invention are the following: The compositions may be built or unbuilt, and may be of the zero-P type (i.e. not containing any phosphorus containing builders). Thus, the composition may contain in the aggregate for example from 1–50%, e.g. at least about 5% and often up to about 35–40% by weight, of one or more organic and/or inorganic builders. Typical examples of builders include those already mentioned above, and more broadly include alkali metal ortho, pyro, and tripolyphosphates, alkali metal carbonates, either alone or in admixture with calcite, alkali metal citrates, alkali metal nitrilotriacetates, carboxymethyloxysuccinates, zeolites, polyacetalcarboxylates, and so on.

More specifically the compositions herein contain from 5% to 20%, preferably from 10% to 15%, by weight of a detergency builder which can be a fatty acid containing from 10 to 18 carbon atoms and/or a polycarboxylate, zeolite, polyphoshonate and/or polyphosphate a builder. Preferred are from 0 to 10% (more preferably from 3% to 10%) by weight of saturated fatty acids containing from 12 to 14 carbon atoms, along with from 0 to 10%, more preferably from 2% to 8%, most preferably from 2% to 5%, by weight of a polycarboxylate builder, most preferably citric acid, in a weight ratio of from 1:1 to 3:1.

Since the proteolytic enzymes herein appear to provide optimum storage stability benefits versus other enzymes when the builder to water hardness ratio is close to one, the compositions preferably contain sufficient builder to sequester from 2 to 10, preferably from 3 to 8, grains per gallon of hardness.

Suitable saturated fatty acids can be obtained from natural sources such as plant or animal esters (e.g., palm kernel oil, palm oil and coconut oil) or synthetically prepared (e.g., via the oxidation of petroleum or by hydrogenation of carbon monoxide via the Fisher-Tropsch process). Examples of suitable saturated fatty acids for use in the compositions of this invention include capric, lauric, myristic, coconut and palm kernel fatty acid. Preferred are saturated coconut fatty acids; from 5:1 to 1:1 (preferably about 3:1) weight ratio mixtures of lauric and myristic acid; mixtures of the above with minor amounts (e.g., 1%–30% of total fatty acid) of oleic acid; and palm kernel fatty acid.

The compositions herein preferably also contain the polycarboxylate, polyphosphonate and polyphosphate builders described in U.S. Pat. No. 4,284,532, Water-soluble polycarboxylate builders, particularly citrates, are preferred of this group. Suitable polycarboxylate builders include the various aminopolycarboxylates, cycloalkane polycarboxylates, ether polycarboxylates, alkyl polycarboxylates, epoxy polycarboxylates, tetrahydrofuran polycarboxylates, benzene polycarboxylates, and polyacetal polycarboxylates.

Examples of such polycarboxylate builders are sodium and potassium ethylenediaminetetraacetate; sodium and potassium nitrilotriacetate; the water-soluble salts of phytic acid, e.g., sodium and potassium phytates, disclosed in U.S. Pat. No. 1,739,942, the polycarboxylate materials described in U.S. Pat. No. 3,364,103; and the water-soluble salts of polycarboxylate polymers and copolymers described in U.S. Pat. No. 3,308,067.

Other useful detergency builders include the water-soluble salts of polymeric aliphatic polycarboxylic acids having the following structural and physical characteristics: (a) a minimum molecular weight of about 350 calculated as to the acid form; (b) an equivalent weight of 50 to 80 calculated as to acid form; (3) at least 45 mole percent of the monomeric species having at least two carboxyl radicals separated from each other by not more than two carbon atoms: (d) the site of attachment of the polymer chain of any carboxyl-containing radical being separated by not more than three carbon atoms along the polymer chain from the site of attachment of the next carboxyl-containing radical. Specific examples of such builders are the polymers and copolymers of itaconic acid, aconitic acid, maleic acid, mesaconic acid, fumaric acid, methylene malonic acid, and citraconic acid.

Other suitable polycarboxylate builders include the water-soluble salts, especially the sodium and potassium salts, of mellitic acid, citric acid, pyromellitic acid, benzene pentacarboxylic acid, oxydiacetic acid, carboxymethyloxysuccinic acid, carboxymethyloxymalonic acid, cis-cyclohexane-hexacarboxylic acid, cis-cyclopentanetetracarboxylic acid and oxydisuccinic acid.

Other polycarboxylates are the polyacetal carboxylates described in U.S. Pat. Nos. 4,144,226, and 4,146,495.

Other detergency builders include the zeolites, such as the aluminosilicate ion exchange material described in U.S. Pat. No. 4,405,483.

Other preferred builders are those of the general formula R—CH(COOH)CH$_2$(COOH), i.e. derivatives of succinic acid, wherein R is $C_{10}$–$C_{20}$ alkyl or alkenyl, preferably $C_{12}$–$C_{16}$, or wherein R may be substituted with hydroxyl, sulfo, sulfoxy or sulfone substituents. These succinate builders are preferably used in the form of their water soluble salts, including the sodium, potassium and alkanolammonium salts. Specific examples of succinate builders include: lauryl succinate, myristyl succinate, palmityl succinate, 2-dodecenyl succinate, and the like.

4. Proteolytic Enzyme

The enzymes of the invention can be used in well-known standard amounts in detergent compositions. The amounts may range very widely, e.g. about 0.0002–0.1, e.g. about 0.005–0.05, Anson units per gram of the detergent composition. Expressed in alternative units, the protease can be included in the compositions in amounts in the order of from about 0.1 to 100 GU/mg (e.g. 1–50, especially 5–20 GU/mg) of the detergent formulation, or any amount in a wide range centering at about 0.01–4, e.g. 0.1–0.4 KNPU per g of detergent formulation.

It may for example be suitable to use the present enzymes at the rate of about 0.25 mg of enzyme protein per liter of wash liquor, corresponding to an enzyme activity of the order of 0.08 KNPU per liter. Corresponding detergent formulations can contain the enzymes in for example an amount of the order of 0.1–0.4 KNPU/g.

Expressed differently the compositions of the present invention contain from about 0.01% to about 5%, preferably from about 0.1% to about 2%, by weight of the proteolytic enzymes of the invention.

The described proteolytic enzyme is preferably included in an amount sufficient to provide an activity of from 0.05 to about 1.0, more preferably from about 0.1 to 0.75, most preferably from about 0.125 to about 0.5 mg of active enzyme per gram of composition.

The enzyme component may be added to the other components in any convenient form, such as in the form of a solution, slurry, LDP slurry, or crystals.

5. Enzyme Stabilization System

The liquid detergents according to the present invention may comprise An enzyme stabilization system, comprising calcium ion, boric acid, propylene glycol and/or short chain carboxylic acids. The enzyme stabilization system comprises from about 0.5% to about 15% by weight of the composition.

The composition preferably contains from about 0.01 to about 50, preferably from about 0.1 to about 30, more preferably from about 1 to 20 millimoles of calcium ion per liter. The level of calcium ion should be selected so that there is always some minimum level available for the enzyme, after allowing for complexation with builders etc. in the composition. Any water-soluble calcium salt can be used as the source of calcium ion, including calcium chloride, calcium formate, and calcium acetate. A small amount of calcium ion, generally from about 0.05 to 0.4 millimoles per liter, is often also present in the composition due to calcium in the enzyme slurry and formula water. From about 0.03% to about 0.6% of calcium formate is preferred.

A second preferred enzyme stabilizer is polyols containing only carbon, hydrogen and oxygen atoms. They preferably contain from 2 to 6 carbon atoms and from 2 to 6 hydroxy groups. Examples include propylene glycol (especially 1,2-propanediol, which is preferred), ethylene glycol, glycerol, sorbitol, mannitol, and glucose. The polyol generally represents from about 0.5% to 15%, preferably from about 1.5% to about 8%, by weight of the composition. Preferably, the weight ratio of polyol to any boric acid added is at least 1, more preferably at least 1.3.

The compositions preferably also contain the water-soluble, short chain carboxylates described in U.S. Pat. No. 4,318,818. The formates are preferred and can be used at levels of from about 0.05% to about 5%, preferably from about 0.2% to about 2%, most preferably from 0.4% to 1.5%, by weight of the composition. Sodium formate is preferred.

The compositions herein also optionally contain from about 0.25% to about 5%, most preferably from about 0.5% to about 3%, by weight of boric acid. The boric acid may be, but is preferably not, formed by a compound capable of forming boric acid in the composition. Boric acid is preferred, although other compounds such as boric oxide, borax and other alkali metal borates (e.g., sodium ortho-, meta- and pyroborate, and sodium pentaborate) are suitable. [Substituted boric acids (e.g., phenylboronic acid, butane boronic acid, and p-bromo phenylboronic acid) can also be used in place of boric acid.

6. Water

The liquid compositions of the present invention may be aqueous liquids or non-aqueous liquids. When the are aqueous liquids, they contain from about 15% to about 60%, preferably from about 25% to about 45%, by weight of water.

FURTHER OPTIONAL COMPONENTS

A. Cosurfactants

Optional cosurfactants for use with the above nonionic surfactants include amides of the formula

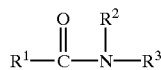

wherein $R^1$ is an alkyl, hydroxyalkyl or alkenyl radical containing from 8 to 20 carbon atoms, and $R^2$ and $R^3$ are selected from the group consisting of hydrogen, methyl, ethyl, propyl, isopropyl, 2-hydroxyethyl, 2-hydroxypropyl, 3-hydroxypropyl, and said radicals additionally containing up to 5 ethylene oxide units, provided at least one of $R^2$ and $R^3$ contains a hydroxyl group.

Preferred amides are the $C_8$–$C_{20}$ fatty acid alkylol amides in which each alkylol group contains from 1 to 3 carbon atoms, and additionally can contain up to 2 ethylene oxide units. Particularly preferred are the $C_{12}$–$C_{16}$ fatty acid monoethanol and diethanol amides.

If used, amides are preferably present at a level such that the above ethoxylated nonionic surfactant and amide surfactant is in a weight ratio of from 4:1 to 1:4, preferably from 3:1 to 1:3.

Preferred and optional cosurfactants, used at a level of from 0.15% to 1%, are the quaternary ammonium, amine and amine oxide surfactants described in U.S. Pat. No. 4,507,219.

Of the above, the $C_{10}$–$C_{14}$ alkyl trimethylammonium salts are preferred, e.g., decyl trimethylammonium methylsulfate, lauryl trimethylammonium chloride, myristyl trimethylammonium bromide, and coconut trimethylammonium chloride and methylsulfate. From 0.2% to 0.8% of monoalkyl trimethylammonium chloride is preferred.

B. Tartrate Succinate Builder

The compositions herein preferably contain from 0 to about 10%, preferably from 0 to about 6%, by weight on an acid basis, of a tartrate succinate builder material selected from the group consisting of:

i)

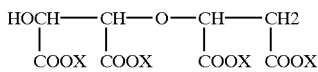

wherein X is a salt-forming cation;

ii)

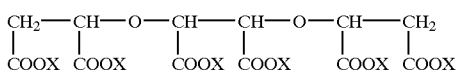

wherein X is a salt-forming cation; and iii) mixtures thereof

The tartrate succinate compounds used herein are described in U.S. Pat. No. 4,663,071.

C. Neutralization System

The present compositions can also optionally contain from about 0 to about 0.04 moles, preferably from about 0.01 to 0.035 moles, more preferably from about 0.015 to about 0.03 moles, per 100 grams of composition of an alkanolamine selected from the group consisting of monoethanolamine, diethanolamine, triethanolamine, and mixtures thereof. Low levels of the alkanolamines, particularly monoethanolamine, are preferred to enhance product stability, detergency performance, and odour. However, the amount of alkanolamine should be minimized for best chlorine bleach compatibility.

In addition, the compositions contain sodium ions, and preferably potassium ions, at a level sufficient to neutralize the anionic species and provide the desired product pH.

D. Suds Suppressor

Another optional component for use in the liquid detergents herein is from 0 to about 1.5%, preferably from about 0.5% to about 1.0%, by weight of silicone based suds suppressor agent.

Silicones are widely known and taught for use as highly effective suds controlling agents. For example, U.S. Pat. No. 3,455,839 relates to compositions and processes for defoaming aqueous solutions by incorporating therein small amounts of polydimethylsiloxane fluids.

Useful suds controlling silicones are mixtures of silicone and silanated silica as described, for instance, in German Patent Application DOS 2,124,526.

Silicone defoamers and suds controlling agents have been successfully incorporated into granular detergent compositions by protecting them from detergent surfactants as in U.S. Pat. Nos. 3,933,672 and 4,652,392.

A preferred silicone based suds suppressor for use herein is a suds suppressing amount of a suds controlling agent consisting essentially of:

(i) polydimethylsiloxane fluid having a viscosity of from about 20 cs. to about 1500 cs. at 25° C.;

(ii) from about 5 to about 50 parts per 100 parts by weight of (i) of siloxane resin composed of $(CH_3)_3 SiO_{1/2}$ units and $SiO_2$ units in a ratio of from $(CH_3)_3 SiO_{1/2}$ units a to $SiO_2$ units of from about 0.6:1 to about 1.2:1; and (iii) from about 1 to about 20 parts per 100 parts by weight of (i) of a solid silica gel.

By "suds suppressing amount" is meant that the formulator of the composition can select an amount of this suds controlling agent that will control the suds to the extent desired. The amount of suds control will vary with the detergent surfactant selected. For example, with high sudsing surfactants, relatively more of the suds controlling agent is used to achieve the desired suds control than with low foaming surfactants.

E. Other Enzymes

The detergent compositions of the invention may also contain further enzymes. For example, lipase can usefully be added in the form of a solution or a slurry of lipolytic enzyme with carrier material (e.g. as in EP 258 068 (Novo Nordisk A/S)).

The added amount of lipase can be chosen within wide limits, for example 50 to 30,000 LU/g per gram of the surfactant system or of the detergent composition, e.g. often at least 100 LU/g, very usefully at least 500 LU/g, sometimes preferably above 1000, above 2000 LU/g or above 4000 LU/g or more, thus very often within the range of 50–4000 LU/g, and possibly within the range of 200–1000 LU/g. In this specification, lipase units are defined as they are in EP 258 068.

The lipolytic enzyme can be chosen among a wide range of lipases. In particular, the lipases described in for example the following patent specifications: EP 214 761 (Novo Nordisk A/S), 258 068, and especially lipases showing immunological cross reactivity with antisera raised against lipase from *Thermomyces lanuginosus* ATCC 22070, EP 205 208 and 206 390, and especially lipases showing immunological cross-reactivity with antisera raised against lipase from *Chromobacter viscosum* var *lipolyticum* NRRL B-3673, or against lipase from Alcaligenes PL-679, ATCC 31371 and FERM-P 3783, also the lipases described in WO 87/00859 (Gist-Brocades) and EP 204 284 (Sapporo Breweries). Suitable, in particular, are for example the following commercially available lipase preparations: Lipolase® Novo Nordisk A/S, Amano lipases CE, P, B, AP, M-AP, AML, and CES, and Meito lipases MY-30, OF, and PL, also Esterase® MM (Novo Nordisk A/S), Lipozym, SP225, SP285, (all Novo Nordisk A/S) Saiken lipase, Enzeco lipase, Toyo Jozo lipase and Diosynth lipase (Trade Marks), Lumafast® (Genencor Inc.), Lipomax® (Gist-Brocades N.V.), and lipases as described in WO 94/03578 (Unilever).

Amylase can for example be used when desired, in an amount in the range of about 1 to about 100 MU (maltose units) per gram of detergent composition (or 0.014–1.4, e.g. 0.07–0.7, KNU/g (Novo units)). Amylases suitable are for example Termamyl®, and BAN (Novo Nordisk A/S). Cellulase can for example be used when desired, in an amount in the range of about 0.3 to about 35 CEVU units per gram of the detergent composition. Suitable cellulases are for example Celluzyme®, and Carezyme® (NOVO NORDISK A/S).

Other enzymes contemplated to be used in the present invention are oxidases and peroxidases F. Other Optional Components Other optional components for use in the liquid detergents herein include soil removal agents, soil release polymers, antiredeposition agents such as tetraethylene pentamine ethoxylate (from about 0.5% to 3%, preferably from about 1% to about 3%, by weight), suds regulants, poly vinyl pyrolidone, carboxy methyl cellulose, clays, and hydrotropes such as sodium cumene sulfonate, opacifiers, antioxidants, bactericides, dyes, perfumes, and brighteners known in the art. Such optional components generally represent less than about 15%, preferably from about 0.5% to 10%, more preferably from about 1% to about 10%, by weight of the composition.

The compositions may contain from 0% to about 8%, preferably from 0% to about 5%, by weight of a $C_{12}$–$C_{14}$ alkenyl succinic acid or salt thereof. These materials are of the general formula R—CH(COOX)CH$_2$(COOX), wherein R is a $C_{12}$–$C_{14}$ alkenyl group and each X is H or a suitable cation, such as sodium, potassium, ammonium or alkanolammonium (e.g., mono-, di-, or tri-ethanolammonium).

Specific examples are 2-dodecenyl succinate (preferred) and 2-tetradecenyl succinate.

The compositions herein optionally contain from about 0.1% to about 1%, preferably from about 0.2% to about 0.6%, by weight of water-soluble salts of ethylenediaminetetramethylenephosphonicacid, diethylenetriaminepentamethylenephosphonic acid, ethylenediamine tetraacetic acid (preferred), or diethylenetriamine pentaacetic acid (most preferred) to enhance cleaning performance when pretreating fabrics.

Furthermore, the detergent compositions may contain from 1–35% of a bleaching agent or a bleach precursor or a system comprising bleaching agent and/or precursor with activator therefor.

Further optional ingredients are lather boosters, anti-corrosion agents, soil-suspending agents, sequestering agents, anti-soil redeposition agents, and so on.

The compositions herein preferably contain up to about 10% of ethanol.

G. Other Properties

The instant composition usually has a pH, in a 10% by weight solution in water at 20° C., of from about 7.0 to 9.0, preferably from about 8.0 to about 8.5.

The instant compositions can also have a Critical Micelle Concentration (CMC) of less than or equal to 200 parts per million (ppm), and an air/water Interfacial Tension above the CMC of less than or equal to 32, preferably less than or equal to about 30, dynes per centimetre at 35° C. in distilled water. These measurements are described in "Measurement of Interfacial Tension and Surface Tension—General Review for Practical Man" C. Weser, *GIT Fachzeitschrift für das Laboratorium*, 24 (1980) 642–648 and 734–742, FIT Verlag Ernst Giebeler, Darmstadt, and "Interfacial Phenomena—Equilibrium and Dynamic Effects", C. A. Miller and P. Neogi, Chapter 1, pp. 29–36 (1985), Marcel Dekker, Inc. New York.

The compositions of the invention can be used for the washing of textile materials, especially, but without limitation cotton and polyester based textiles and mixtures thereof. For example washing processes carried out at temperatures of about 60–65° C. or lower, e.g. about 30–35° C. or lower, are particularly suitable. It can be very suitable to use the compositions at a rate sufficient to provide about e.g. 0.4–0.8 g/l of surfactant in the wash liquor, although it is of course possible to use lower or higher concentrations, if desired. Without limitation it can for example be stated that a use-rate from about 1 to 10 g/l, e.g. from about 3–6 g/l, of the detergent formulation is suitable for use in the case when the formulations are substantially as in the Examples.

In this aspect the invention is especially related to:

a) A detergent composition formulated as an aqueous detergent liquid comprising anionic surfactant, non-ionic surfactant, humectant, organic acid, caustic alkali, with a pH adjusted to a value between 9 and 10.

b) A detergent composition formulated as a non-aqueous detergent liquid comprising a liquid nonionic surfactant consisting essentially of linear alkoxylated primary alcohol, triacetin, sodium triphosphate, caustic alkali, perborate monohydrate bleach precursor, and tertiary amine bleach activator, with a pH adjusted to a value between about 9 and 10.

c) An enzymatic liquid detergent composition formulated to give a wash liquor pH of 9 or less when used at a rate corresponding to 0.4–0.8 g/l surfactant.

d) An enzymatic liquid detergent composition formulated to give a wash liquor pH of 8.5 or more when used at a rate corresponding to 0.4–0.8 g/l surfactant.

e) An enzymatic liquid detergent composition formulated to give a wash liquor ionic strength of 0.03 or less, e.g. 0.02 or less, when used at a rate corresponding to 0.4–0.8 g/l surfactant.

f) An enzymatic liquid detergent composition formulated to give a wash liquor ionic strength of 0.01 or more, e.g. 0.02 or more, when used at a rate corresponding to 0.4–0.8 g/l surfactant.

It was found that the subtilase variants of the present invention can also be usefully incorporated in detergent composition in the form of bars, tablets, sticks and the like for direct application to fabrics, hard surfaces or any other surface. In particular, they can be incorporated into soap or soap/synthetic compositions in bar form, wherein they exhibit a remarkable enzyme stability. Detergent composition in the form of bars, tablets, sticks and the like for direct application, are for example described in South African Patent 93/7274, incorporated herein by reference.

Accordingly, the preferred bars in accordance with this invention comprise, in addition to the subtilase variant:

i) 25 to 80%, most preferably 25 to 70%, by weight of detergent active which is soap or a mixture of soap and synthetic detergent active, reckoned as anhydrous;

ii) 0 to 50 % and, most preferably, 10 to 30% by weight of water;

iii) 0 to 35% and, most preferably, 0.1 to 30% by weight filler.

In general, the amount of subtilase variant to be included in such compositions of the invention is such that it corresponds with a proteolytic activity of 0.1 to 100 GU/mg based on the composition, preferably 0.5 to 20GU/mg, most preferably 1.0 to 10 GU/mg, where GU/mg is glycine unit per milligram.

METHOD FOR PRODUCING MUTATIONS IN SUBTILASE GENES

Many methods for introducing mutations into genes are well known in the art. After a brief discussion of cloning subtilase genes, methods for generating mutations in both random sites, and specific sites, within the subtilase gene will be discussed.

CLONING A SUBTILASE GENE

The gene encoding a subtilase may be cloned from any of the organisms indicated in Table I, especially gram-positive bacteria or fungus, by various methods, well known in the art. First a genomic, and/or cDNA library of DNA must be constructed using chromosomal DNA or messenger RNA from the organism that produces the subtilase to be studied. Then, if the amino-acid sequence of the subtilase is known, homologous, labelled oligonucleotide probes may be synthesized and used to identify subtilisin-encoding clones from a genomic library of bacterial DNA, or from a cDNA library. Alternatively, a labelled oligonucleotide probe containing sequences homologous to subtilase from another strain of bacteria or organism could be used as a probe to identify subtilase-encoding clones, using hybridization and washing conditions of lower stringency.

Yet another method for identifying subtilase-producing clones would involve inserting fragments of genomic DNA into an expression vector, such as a plasmid, transforming protease-negative bacteria with the resulting genomic DNA library, and then plating the transformed bacteria onto agar containing a substrate for subtilase, such as skim milk. Those bacteria containing subtilase-bearing plasmid will produce colonies surrounded by a halo of clear agar, due to digestion of the skim milk by excreted subtilase.

GENERATION OF RANDOM MUTATIONS IN THE SUBTILASE GENE

Once the subtilase gene has been cloned into a suitable vector, such as a plasmid, several methods can be used to introduce random mutations into the gene.

One method would be to incorporate the cloned subtilase gene, as part of a retrievable vector, into a mutator strain of *Eschericia coli*.

Another method would involve generating a single stranded form of the subtilase gene, and then annealing the fragment of DNA containing the subtilase gene with another DNA fragment such that a portion of the subtilase gene remained single stranded. This discrete, single stranded region could then be exposed to any of a number of mutagenizing agents, including, but not limited to, sodium bisulfite, hydroxylamine, nitrous acid, formic acid, or hydralazine. A specific example of this method for generating random mutations is described by Shortle and Nathans (1978, *Proc. Natl. Acad. Sci. U.S.A.*, 75 2170–2174). According to the shortle and Nathans method, the plasmid bearing the subtilase gene would be nicked by a restriction enzyme that cleaves within the gene. This nick would be widened into a gap using the exonuclease action of DNA polymerase I. The resulting single-stranded gap could then be mutagenized using any one of the above mentioned mutagenizing agents.

Alternatively, the subtilisin gene from a Bacillus species including the natural promoter and other control sequences could be cloned into a plasmid vector containing replicons for both *E. coli* and *B. subtilis*, a selectable phenotypic marker and the M13 origin of replication for production of single-stranded plasmid DNA upon superinfection with helper phage IR1. Single-stranded plasmid DNA containing the cloned subtilisin gene is isolated and annealed with a DNA fragment containing vector sequences but not the coding region of subtilisin, resulting in a gapped duplex molecule. Mutations are introduced into the subtilisin gene either with sodium bisulfite, nitrous acid or formic acid or by replication in a mutator strain of *E. coli* as described above. Since sodium bisulfite reacts exclusively with cytosine in a single-stranded DNA, the mutations created with this mutagen are restricted only to the coding regions. Reaction time and bisulfite concentration are varied in different experiments such that from one to five mutations are created per subtilisin gene on average. Incubation of 10 $\mu$g of gapped duplex DNA in 4 M Na-bisulfite, pH. 6.0, for 9 minutes at 37° C. in a reaction volume of 400 $\mu$l, deaminates about 1% of cytosines in the single-stranded region. The coding region of mature subtilisin contains about 200 cytosines, depending on the DNA strand. Advantageously, the reaction time is varied from about 4 minutes (to produce a mutation frequency of about one in 200) to about 20 minutes (about 5 in 200).

After mutagenesis the gapped molecules are treated in vitro with DNA polymerase I (Klenow fragment) to make fully double-stranded molecules and fix the mutations. Competent *E. coli* are then transformed with the mutagenized DNA to produce an amplified library of mutant subtilisins. Amplified mutant libraries can also be made by growing the plasmid DNA in a Mut D strain of *E. coli* which increases the range of mutations due to its error prone DNA polymerase.

The mutagens nitrous acid and formic acid may also be used to produce mutant libraries. Because these chemicals are not as specific for single-stranded DNA as sodium bisulfite, the mutagenesis reactions are performed according to the following procedure. The coding portion of the subtilisin gene is cloned in M13 phage by standard methods and single stranded phage DNA prepared. The single-stranded DNA is then reacted with 1 M nitrous acid pH. 4.3 for 15–60 minutes at 23° C. or 2.4 M formic acid for 1–5 minutes at 23° C. These ranges of reaction times produce a mutation frequency of from 1 in 1000 to 5 in 1000. After mutagenesis, a universal primer is annealed to the M13 DNA and duplex DNA is synthesized using the mutagenized single-stranded DNA as a template so that the coding portion of the subtilisin gene becomes fully double-stranded. At this point the coding region can be cut out of the M13 vector with restriction enzymes and ligated into an un-mutagenized expression vector so that mutations occur only in the restriction fragment. (Myers et al., *Science* 229 242–257 (1985)).

GENERATION OF SITE DIRECTED MUTATIONS IN THE SUBTILASE GENE

Once the subtilase gene has been cloned, and desirable sites for mutation identified and the residue to substitute for the original ones have been decided, these mutations can be introduced using synthetic oligonucleotides. These oligonucleotides contain nucleotide sequences flanking the desired mutation sites; mutant nucleotides are inserted during oligonucleotide synthesis. In a preferred method, a single stranded gap of DNA, bridging the subtilase gene, is created in a vector bearing the subtilase gene. Then the synthetic nucleotide, bearing the desired mutation, is annealed to a homologous portion of the single-stranded DNA. The remaining gap is then filled in by DNA polymerase I (Klenow fragment) and the construct is ligated using T4 ligase. A specific example of this method is described in Morinaga et al., (1984, *Biotechnology* 2 646–639). According to Morinaga et al., a fragment within the gene is removed using restriction endonuclease. The vector/gene, now containing a gap, is then denatured and hybridized to a vector/gene which, instead of containing a gap, has been cleaved with another restriction endonuclease at a site outside the area involved in the gap. A single-stranded region of the gene is then available for hybridization with mutated oligonucleotides, the remaining gap is filled in by the Klenow fragment of DNA polymerase I, the insertions are ligated with T4 DNA ligase, and, after one cycle of replication, a double-stranded plasmid bearing the desired mutation is produced. The Morinaga method obviates the additional manipulation of constructing new restriction sites, and therefore facilitates the generation of mutations at multiple sites. U.S. Reissue Pat. No. 34,606 by Estell et al., issued May 10, 1994, is able to introduce oligonucleotides bearing multiple mutations by performing minor alterations of the cassette, however, an even greater variety of mutations can be introduced at any one time by the Morinaga method, because a multitude of oligonucleotides, of various lengths, can be introduced.

EXPRESSION OF SUBTILASE MUTANTS

According to the invention, a mutated subtilase gene produced by methods described above, or any alternative methods known in the art, can be expressed, in enzyme form, using an expression vector. An expression vector generally falls under the definition of a cloning vectors since an expression vector usually includes the components of a typical cloning vector, namely, an element that permits autonomous replication of the vector in a microorganism independent of the genome of the microorganism, and one or more phenotypic markers for selection purposes. An expression vector includes control sequences encoding a promoter, operator, ribosome binding site, translation initiation signal, and, optionally, a repressor gene or various activator genes. To permit the secretion of the expressed protein, nucleotides encoding a "signal sequence" may be inserted prior to the coding sequence of the gene. For expression under the direction of control sequences, a target gene to be treated according to the invention is operably linked to the control sequences in the proper reading frame. Promoter sequences that can be incorporated into plasmid vectors, and which can support the transcription of the mutant subtilase gene, include but are not limited to the prokaryotic β-lactamase promoter (Villa-Kamaroff, et al. (1978) *Proc. Natl. Acad. Sci. U.S.A.* 75 3727–3731) and the tac promoter (DeBoer, et al. (1983) *Proc. Natl. Acad. Sci. U.S.A.* 80 21–25). Further references can also be found in "Useful proteins from recombinant bacteria" in *Scientific American* (1980) 242 74–94.

According to one embodiment *B. subtilis* is transformed by an expression vector carrying the mutated DNA. If expression is to take place in a secreting microorganism such as *B. subtilis* a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when it is present.

Other host systems known to the skilled person are also contemplated for the expression and production of the protease variants of the invention. Such host systems comprise fungi, including filamentous fungi, plant, avian and mammalian cells, as well as others.

MATERIALS AND METHODS

Strains

*B. subtilis* 309 and 147 are variants of *Bacillus lentus*, deposited with the NCIB and accorded the accession numbers NCIB 10309 and 10147, and described in U.S. Pat. No. 3,723,250 incorporated by reference herein.

*E. coli* MC 1000 (M. J. Casadaban and S. N. Cohen (1980); *J. Mol. Biol.* 138 179–207), was made r$^-$m$^+$ by conventional methods and is also described in U.S. Patent application Ser. No. 039,298.

Proteolytic Activity

In the context of this invention proteolytic activity is expressed in Kilo NOVO Protease Units (KNPU). The activity is determined relatively to an enzyme standard (SAVINASE™), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novo Nordisk A/S, Denmark, which folder is hereby included by reference.

A GU is a Glycine Unit, defined as the proteolytic enzyme activity which, under standard conditions, during a 15-minutes' incubation at 40 deg C, with N-acetyl casein as substrate, produces an amount of $NH_2$-group equivalent to 1 μmole of glycine.

Enzyme activity can also be measured using the PNA assay, according to reaction with the soluble substrate succinyl-alanine-alanine-proline-phenyl-alanine-para-nitrophenol, which is described in the Journal of American Oil Chemists Society, Rothgeb, T. M., Goodlander, B. D., Garrison, P. H., and Smith, L. A., (1988).

EXAMPLES

For the generation of enzyme variants according to the invention the same materials and methods as described in i.a. WO 89/06279 (Novo Nordisk A/S), EP 130,756 (Genentech), EP 479,870 (Novo Nordisk A/S), EP 214,435 (Henkel), WO 87/04461 (Amgen), WO 87/05050 (Genex), EP application no. 87303761 (Genentech), EP 260,105 (Genencor), WO 88/06624 (Gist-Brocades N.V.), WO 88/07578 (Genentech), WO 88/08028 (Genex), WO 88/08033 (Amgen), WO 88/08164 (Genex), Thomas et al. (1985) *Nature*, 318 375–376; Thomas et al. (1987) *J. Mol. Biol.*, 193, 803–813; Russel and Fersht (1987) *Nature* 328 496–500. Other methods well established in the art may also be used.

Example 1

Construction and Expression of Enzyme Variants

A vector suited to a synthetic gene coding for subtilase 309 and its mutants was constructed. It is essentially a pUC19 plasmid [Yanish-Perron and Messing (1985) *Gene*; 33 103–119], in which the multiple cloning site has been replaced by a linker containing the restriction sites used to separate five sub-fragments constituting the gene. The new linker was inserted into EcoRI—HindIII cut pUC19 thereby destroying these sites. The details of this construction are described in WO 92/19729 on pages 25–26 and in FIG. 1 (sheets 1/7–7/7) thereof, the content of which is hereby included by reference.

Each subfragment was made from 6 to 12 oligonucleotides. The oligonucleotides were synthesised on an automatic DNA synthesizer using phosphoramidite chemistry on a controlled glass support [Beaucage and Carruthers (1981); *Tetrahedron Letters* 22 1859–1869].

The five subfragments were isolated on a 2% agarose gel and inserted into pSX191. The sequence was verified by dideoxynucleotide sequencing. Fragments A–E were isolated and ligated together with KpnI-BamHI cut pSX191. The ligation mixtures were used to transform competent *E. coli* MC1000 r$^-$,m$^+$ selecting for ampicillin resistance. The 850 bp KpnI-BamHI fragment that constitutes the part of the subtilisin 309 gene coding for the mature part of the enzyme was then used to replace the wild type gene on pSX212 giving rise to pSX222, which was then transformed into a competent *B. subtilis* strain. After fermentation of the transformed strain and purification of the enzyme it was shown that the product was indistinguishable from the wild type product.

Protease variants derived from the synthetic gene are made by using oligonucleotides with altered sequence at the place(s) where mutation is wanted (e.g. with sequences as given below) and mixing them with the rest of the oligonucleotides appropriate to the synthetic gene. Assembly of the variant gene is carried out with the variant materials in a manner otherwise analogous to that described above. Further information on synthetic genes generally is available in Agarval et al. (1970); *Nature*; 227 27–34.

A KpnI site was introduced into the beginning of the subtilase 309 synthetic gene encoding the mature part of the enzyme. The method used is called oligonucleotide directed double-strand break repair mutagenesis and is described by Mandecki (1986) *Proc. Nat. Acad. Sci. USA* 83 7177–7181. pSX172 is opened with NcoI at the beginning of the mature part of the subtilase 309 gene and is mixed with the oligonucleotide NOR 789 (see WO 92/19729), heated to 100° C., cooled to 0° .C, and transformed into *E. coli*. After retansformation, the recombinants can be screened by colony hybridisation using 32-P-labelled NOR 789. The recombinants that turned out to be positive during the screening had the KpnI site introduced right in front of NcoI by changing two bases without changing the amino acid sequence. pSX172 is described in EP 405 901. The KpnI site so created is inserted into pSX120 on a 400-bp PvuI-NheI fragment, giving rise to pSX212. pSX120 is also described in EP 405 901.

The synthetic gene is inserted between KpnI and BamHI on pSX212, giving rise to pSX222.

Examples of mutations and corresponding sequences of oligonucleotides are as follows:

R170L (fragment D1)

```
5'-AATTCAGGTGCAGGCTCAATCAGCTATCCGGCGCTCTAT-3'
   |||||||||||||||||||||||||||||||||*||||
      5'-  GTCCACGTCCGAGTTAGTCGATAGGCCGCGAGATACGC-
                                               TTG-3'
```

R170I (fragment D1)

```
5'-AATTCAGGTGCAGGCTCAATCAGCTATCCGGCGATCTAT-3'
   |||||||||||||||||||||||||||||||||**||||
      5'-  GTCCACGTCCGAGTTAGTCGATAGGCCGCTAGATACGC-
                                               TTG-3'
```

S57P (fragment B1)

```
5'-AGCTTTGTACCAGGGGAACCGCCGACTCAAGATGGG-3'
   |||||||||||||||||*||||||||||||||||
      3'-  AACATGGTCCCCTTGGCGGCTGAGTTCTACCCTTACCC-5'
```

These oligonucleotides were combined with the rest of the oligonucleotides from the synthetic gene that was not changed.

Example 2

Purification of Enzyme Variants

This procedure relates to purification of a 10 liter scale fermentation of the Subtilisin 147 enzyme, the Subtilisin 309 enzyme or mutants thereof.

Approximately 8 liters of fermentation broth were centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 400 ml using an Amicon CH2A UF unit equipped with an Amicon S1Y10 UF cartridge. The UF concentrate was centrifuged and filtered prior to absorption at room temperature on a Bacitracin affinity column at pH 7. The protease was eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to a 750 ml Sephadex G25 column (5 cm dia.) equilibrated with a buffer containing 0.01 dimethylglutaric acid, 0.2 M boric acid and 0.002 m calcium chloride adjusted to pH 6 5.

Fractions with proteolytic activity from the Sephadex G25 column were combined and applied to a 150 ml CM Sepharose CL 6B cation exchange column (5 cm dia.) equilibrated with a buffer containing 0.01 M dimethylglutaric acid, 0.2 M boric acid, and 0.002 M calcium chloride adjusted to pH 6.5.

The protease was eluted using a linear gradient of 0–0.1 M sodium chloride in 2 liters of the same buffer (0–0.2 M sodium chloride in case of Subtilisin 147).

In a final purification step protease containing fractions from the CM Sepharose column were combined and concentrated in an Amicon ultrafiltration cell equipped with a GR81PP membrane (from the Danish Sugar Factories Inc.).

By using the techniques of Example 1 for the construction and the above isolation procedure the following subtilisin 309 variants were produced and isolated:

| | |
|---|---|
| A: | G159I |
| B: | S164I |
| C: | Y167I |
| D: | R170I |
| E: | R170L |
| F: | R170M |
| G: | R170F |
| H: | G195F |
| I: | S57P + R170L |
| J: | R170L + N218S |
| K: | S57P + R170L + N218S |
| L: | R170L + N218S + M222A |
| M: | S57P + R170L + S188P + A194P |
| N: | Y167I + R170L |
| O: | S57P + R170L + Q206E |
| P: | R170L + Q206E |
| Q: | Y167I + R170L + Q206E |
| R: | Y167I + R170L + A194P |
| S: | Y167I + R170L + N218S |
| T: | Y167I + R170L + A194P + N218S |
| U: | Y167I + Y171I |
| V: | R170G |
| W: | R170C |
| X: | Y171I |
| Y: | Y167I + R170L + N218S |

Example 3

Stability in Detergent Compositions Comprising Enzyme Variants

Example D1

An (isotropic) aqueous detergent liquid according to an embodiment of the invention is formulated to contain:

| Ingredient | % |
|---|---|
| NaLAS | 8.0 |
| Neodol 25-9 | 8.0 |
| AES 25-3S | 14.0 |
| NaCitrate.2H$_2$O | 5.0 |
| Propylene Glycol | 5.0 |
| Sorbitol | 4.5 |
| F-dye Tinopal UNPA-GX | 0.15 |

-continued

| Ingredient | % |
|---|---|
| Lytron 614 Opacifier | 0.03 |
| Kathon Preservative | 0.0003 |
| Acid Blue 80 | 0.00117 |
| Acid Violet 48 | 0.0033 |
| SAVINASE ® 16L | 0.25 |
| LIPOLASE ® 100L | 0.70 |
| Fragrance | 0.15 |
| Water | ad 100.0 |

The pH is adjusted to 7.1.

Table III—Residual enzyme activity (in percentage of original activity) after storage at 37° C. for Example D1 comprising the BLS309 variant S57P+R170L+N218S.

| Storage time (days) | Wild-type | S57P + R170L + N218S |
|---|---|---|
| 0 | 100 | 100 |
| 3 | 44 | 74 |
| 7 | 11 | 50 |
| 10 | 5 | 36 |
| 14 | 7 | 27 |

From Table III it is evident that the variant S57P+R170L+N218S exhibits a remarkably improved stability in this type of detergent. Moreover, the variant S57P+R170L+N218S possesses excellent compatibility towards lipase.

Table IV—Residual lipase activity (in percentage of original activity) after storage at 37° C. for Example D1 comprising the BLS309 variant S57P+R170L+N218S and LIPOLASE®. Storage time (days)

| LIPOLASE ® plus: | Wild-type | S57P + R170L + N218S |
|---|---|---|
| 0 | 100 | 100 |
| 3 | 38 | 67 |
| 7 | 24 | 44 |
| 10 | 22 | 33 |
| 14 | 21 | 27 |

From Table IV it is apparent that, in addition to the stability of the protease, the compatibility of the protease is also improved.

Example D2

A non-aqueous detergent liquid according to an embodiment of the invention is formulated using 38.5% $C_{13}$–$C_{15}$ linear primary alcohol alkoxylated with 4.9 mol/mol ethylene oxide and 2.7 mol/mol propylene oxide, 5% triacetin, 30% sodium triphosphate, 4% soda ash, 15.5% sodium perborate monohydrate containing a minor proportion of oxoborate, 4% TAED, 0.25% EDTA of which 0.1% as phosphonic acid, Aerosil 0.6%, SCMC 1%, and 0.6% protease. The pH is adjusted to a value between 9 and 10, e.g. about 9.8.

Example D3

Structured liquid detergents can for example contain, in addition to a protease as described herein, 2–15% nonionic surfactant, 5–40% total surfactant, comprising nonionic and optionally anionic surfactant, 5–35% phosphate-containing or non-phosphate containing builder, 0.2–0.8% polymeric thickener, e.g. cross-linked acrylic polymer with m.w. over $10^6$, at least 10% sodium silicate, e.g. as neutral waterglass, alkali (e.g. potassium-containing alkali) to adjust to desired pH, preferably in the range 9–10 or upwards, e.g. above pH 11, with a ratio sodium cation: silicate anion (as free silica) (by weight) less than 0.7:1, and viscosity of 0.3–30 Pas (at 20° C. and $20^{s-1}$).

Suitable examples contain about 5% nonionic surfactant $C_{13-15}$ alcohol alkoxylated with about 5 EO groups per mole and with about 2.7 PO groups per mole, 15–23% neutral waterglass with 3.5 weight ratio between silica and sodium oxide, 13–19% KOH, 8–23% STPP, 0–11% sodium carbonate, 0.5% Carbopol 941 (TM).

Protease may be incorporated at for example 0.5%.

Example D4

| (Decoupling polymer liquid) | |
|---|---|
| Priolene 6907 | 4.5 |
| KOH | 10 |
| Ethoxylated Alcohol.7EO (Synperonic A7) | 4.5 |
| Ethoxylated Alcohol.3EO (Synperonic A3) | 4.5 |
| Zeolite 4A | 15 |
| Fluorescer Tinopal CBS-X | 0.08 |
| Narlex DC1 | 1 |
| Citric acid | 8.23 |
| Antifoam silicone DB100 | 0.3 |
| LAS acid | 16.5 |
| Perfume | 0.5 |
| Water to | 100 |

Table V—Residual enzyme activity (in percentage of original activity) after storage at 37° C. for Example D4 comprising the R170L variant of BLS309.

| Storage time (days) | R170L | Wild-type |
|---|---|---|
| 0 | 100 | 100 |
| 2 | 98 | 73 |
| 4 | 96 | 66 |
| 10 | 94 | 46 |
| 33 | 87 | 8 |
| 81 | 78 | 2.1 |
| 101 | 71 | 0 |

From Table V it is evident that the R170L variant exhibits a remarkably improved stability in this type of detergent.

TABLE VI

| Storage (days) | Enzyme | WT | R170M | S57P + R170L + Q206E | Y1671 + R170L + N218S |
|---|---|---|---|---|---|
| 0 | | 100 | 100 | 100 | 100 |
| 0.1 | | 90.2 | 78 | 97 | 94 |
| 1 | | 58 | 53 | 95 | 68 |
| 2 | | 40 | 34 | 87 | 55 |
| 5 | | 16 | 27 | 75 | 29 |
| 6 | | 12 | 22 | 73 | 24 |
| 8 | | 8 | 19 | 77 | 17 |
| 14 | | 2 | 11 | 52 | 4 |

From Table VI it can be seen that the variants tested exhibit improved stability in comparison to the wild type enzyme in this type of detergent Example D5

| (Decoupling polymer liquid) | |
| --- | --- |
| Priolene 6907 | 4.5 |
| KOH | 10 |
| Ethoxylated Alcohol.7EO (Synperonic A7) | 4.5 |
| Ethoxylated Alcohol.3EO (Synperonic A3) | 4.5 |
| Zeolite 4A | 15 |
| Fluorescer Tinopal CBS-X | 0.08 |
| Narlex DC1 | 1 |
| Citric acid | 8.23 |
| Antifoam silicone DB100 | 0.3 |
| LAS acid | 16.5 |
| Lipolase ® 100 L | 0.6 |
| Perfume | 0.5 |
| Water to | 100 |

Table VII—Residual enzyme activity (in percentage of original activity) after storage at 37° C. for Example D5 comprising the BLS309 variant S57P+R170L+N218S.

| | Residual protease activity | Residual lipase activity | | |
| --- | --- | --- | --- | --- |
| Storage time (days) | S57P + R170L + N218S | Wild-type | R170L | S57P + R170L + N218S |
| 0 | 100 | 100 | 100 | 100 |
| 2 | — | 27 | 41 | 94 |
| 5 | 97 | 9 | 15 | 76 |
| 8 | 87 | 4 | 7 | 71 |
| 12 | 91 | 2.4 | 12 | 78 |
| 28 | 100 | 2.4 | 12 | 70 |

From Table VII it is evident that the variant S57P+R170L+N218S exhibits a remarkably improved stability in this type of detergent. Moreover the variant S57P+R170L+N218S possesses excellent compatibility towards lipase.

Example D6

Soap bars were produced containing 49.7 wt. 80/20 tallow/coconut soap, 49.0% water, 20% sodium citrate, 1.0% citric acid and 0.031% protease. After preparation of the soap bars they were stored at ambient temperature and after specific time intervals samples were taken and measured for protease activity. The stability data are given below:

TABLE VIII

| Storage (days) | Enzyme WT | R170L | R170L + N218S + S57P | R170L + Y167I |
| --- | --- | --- | --- | --- |
| 0 | 100 | 100 | 100 | 100 |
| 1 | 50 | 100 | 97 | 94 |
| 2 | 25 | 91 | 100 | 83 |
| 3 | — | 100 | 94 | 80 |
| 6 | — | 98 | 89 | 90 |
| 10 | — | 0 | 100 | 94 | 71 |
| 17 | — | | 93 | 80 | 73 |
| 27 | — | | 95 | 86 | 70 |

From Table VIII it is evident that the subtilase variants R170L, R170L+N218S+S57P and R170L+Y167I exhibit a remarkably improved stability in this type of detergent.

Example D7

Soap bars were produced containing 63.88% 80/20 tallow/coconut soap, 1% coconut fatty acid, 25.1% water, 10% sodium citrate and 0.021% protease. The laundry soap bars were stored at 37° C. and after specific time intervals samples were taken and measured for protease activity.

TABLE IX

| | Stability data: | | |
| --- | --- | --- | --- |
| Storage (days) | Enzyme | WT | R170L + N218S + S57P |
| 0 | | 100 | 100 |
| 10 | | 10 | 90.1 |
| 14 | | — | 81.5 |
| 20 | | 0 | 91.4 |
| 31 | | — | 72.8 |
| 35 | | — | 79 |
| 45 | | — | 78 |

From Table IX it is evident that the subtilase variant R170L+N218S+S57P exhibits a remarkably improved stability in this type of detergent.

Example 4

Wash Performance of Detergent Compositions Comprising Enzyme Variants

The following examples provide results from a number of washing tests that were conducted under the conditions indicated.

Experimental Conditions

TABLE X

| Experimental conditions for evaluation of Subtilisin 309 variants. | |
| --- | --- |
| Detergent | Protease model detergent '95 |
| Detergent dose | 3 g/l |
| pH | 9.5 |
| Wash time | 15 min. |
| Temperature | 15° C. |
| Water hardness | 9° dH~1.61 mM $Ca^{2+}$/$Mg^{2+}$ |
| Enzymes | Subtilisin 309 variants as listed below |
| Enzyme conc. | 0; 0.1, 0.2, 0.3, 0.4, 0.5, 1.0, 2.0, 3.0 mg/l |
| Test system | 150 ml beakers with a stirring rod. |
| Cloth/volume | 5 cloths (Ø 2.5 cm)/50 ml Detergent solution. |
| Cloth | Cotton soiled with grass juice |

Subsequent to washing the cloths were flushed in tap water and air-dried.

The above model detergent is a simple detergent formulation. The most characteristic features are that STP is used as builder and the content of anionic tenside (LAS) is quite high. Further the pH is adjusted to 9.5, which is low for a powder detergent.

TABLE XI

| The composition of the model detergent is as follows: | |
| --- | --- |
| 25% | STP ($Na_5P_3O_{10}$) |
| 25% | $Na_2SO_4$ |
| 10% | $Na_2CO_3$ |
| 20% | LAS (Nansa 80S) |
| 5% | NI (Dobanol 25-7) |
| 5% | $Na_2Si_2O_5$ |
| 0.5% | Carboxymethylcellulose (CMC) |
| 9.5% | water | dose: 3 g/l
pH is adjusted to 9.5
Measurement of remission (R) on the test material has been done at 460 nm using an Elrepho 2000 photometer (without UV). The measured values have been fitted to the expression:

$$\Delta R = \frac{a \cdot \Delta R_{max} \cdot c}{\Delta R_{max} + a \cdot c}$$

The improvement factor is calculated by use of the initial slope of the curve:

$$IF = \frac{a}{a_{ref.}}$$

ΔR is the wash effect of the enzyme in remission units.
a is the initial slope of the fitted curve (c→0).
$a_{ref.}$ is the initial slope for the reference enzyme.
c is the enzyme concentration in mg/l
$\Delta R_{max}$ is the theoretical maximum wash effect of the enzyme in remission units (c→∞).

TABLE XII

Variants and improvement factors for Subtilisin 309.

| Designation | Variant | IF |
|---|---|---|
| S003* | R170Y | 2.8 |
| S004* | R170Y + G195E | 2.6 |
| S012* | R170Y + G195E + K251E | 1.6 |
| G | R170F | 3.3 |
| E | R170L | 3.8 |
| F | R170M | 2.4 |
| D | R170I | 4.1 |
| I | S57P + R170L | 3.9 |
| J | R170L + N218S | 1.6 |
| K | S57P + R170L + N218S | 2.3 |
| N | Y167I + R170L | 6.2 |
| P | R170L + Q206E | 2.6 |

TABLE XII-continued

Variants and improvement factors for Subtilisin 309.

| Designation | Variant | IF |
|---|---|---|
| V | R170G | 2.0 |
| W | R170C | 3.4 |
| O | S57P + R170L + Q206E | 2.9 |
| Q | Y167I + R170L + Q206E | 2.4 |
| R | Y167I + R170L + A194P | 5.1 |
| X | Y171I | 1.2 |
| Y | Y167I + R170L + N218S | 4.0 |
| T | Y167I + R170I + A194P + N218S | 3.6 |

*Described in WO 91/00345

As it can be seen from Table XII all the Subtilisin 309 variants of the invention exhibits an improvement in wash performance.

TABLE XIII

Variants and improvement factors for Subtilisin 309 in a detergent as described in Example D4

| Designation | Variant | IF |
|---|---|---|
| S003* | R170Y | 1.5 |
| F | R170M | 1.2 |
| O | S57P + R170L + Q206E | 5.0 |
| X | Y171I | 4.2 |
| R | Y167I + R170L + A194P | 1.2 |
| T | Y167I + R170L + A194P + N218S | 2.0 |
| Y | Y167I + RI70L + N218S | 2.3 |

*Described in WO 91/00345

As it can be seen from Table XIII all the Subtilisin 309 variants of the invention exhibits an improvement in wash performance.

---

We claim:

1. A modified subtilisin 309 comprising one or both of the following substitutions:
   (a) Y167A, Y167C, Y167G, Y167H, Y167I, Y167L, Y167M, Y167N, Y167P, Y167Q, Y167S, Y167T, or Y167W, and
   (b) R170A, R170C, R170F, R170G, R170H, R170I, R170L, R170M, R170N, R170P, R170S, R170T, R170V, or R170W, wherein each position corresponds to a position of the amino acid sequence of subtilisin BPN'.

2. The modified subtilisin 309 of claim 1, which comprises Y167A.

3. The modified subtilisin 309 of claim 1, which comprises Y167C.

4. The modified subtilisin 309 of claim 1, which comprises Y167G.

5. The modified subtilisin 309 of claim 1, which comprises Y167H.

6. The modified subtilisin 309 of claim 1, which comprises Y167I.

41

7. The modified subtilisin 309 of claim 1, which comprises Y167L.

8. The modified subtilisin 309 of claim 1, which comprises Y167M.

9. The modified subtilisin 309 of claim 1, which comprises Y167N.

10. The modified subtilisin 309 of claim 1, which comprises Y167P.

11. The modified subtilisin 309 of claim 1, which comprises Y167Q.

12. The modified subtilisin 309 of claim 1, which comprises Y167S.

13. The modified subtilisin 309 of claim 1, which comprises Y167T.

14. The modified subtilisin 309 of claim 1, which comprises Y167V.

15. The modified subtilisin 309 of claim 1, which comprises Y167W.

16. The modified subtilisin 309 of claim 1, which comprises R170A.

17. The modified subtilisin 309 of claim 1, which comprises R170C.

18. The modified subtilisin 309 of claim 1, which comprises R170F.

19. The modified subtilisin 309 of claim 1, which comprises R170G.

20. The modified subtilisin 309 of claim 1, which comprises R170H.

21. The modified subtilisin 309 of claim 1, which comprises R170I.

22. The modified subtilisin 309 of claim 1, which comprises R170L.

23. The modified subtilisin 309 of claim 1, which comprises R170M.

24. The modified subtilisin 309 of claim 1, which comprises R170N.

25. The modified subtilisin 309 of claim 1, which comprises R170P.

26. The modified subtilisin 309 of claim 1, which comprises R170Q.

27. The modified subtilisin 309 of claim 1, which comprises R170S.

28. The modified subtilisin 309 of claim 1, which comprises R170T.

29. The modified subtilisin 309 of claim 1, further comprising at least one further mutation at one or more of positions: 27, 36, 57, 76, 97, 101, 104, 120, 123, 206, 218, 222, 224, 235 and 274.

30. The modified subtilisin 309 of claim 31, wherein at least one further mutation is selected from the group consisting of K27R, *36D, S57P, N76D, G97N, S101G, V104A, V104N, V104Y, H120D, N123S, A194P, Q206E, N218S, M222A, M222S, T224S, K235L, and T274A.

31. A detergent composition comprising a modified subtilisin 309 of claim 1 and a surfactant.

32. The detergent composition of claim 32, wherein the composition is in solid powdered form.

33. The detergent composition of claim 32, wherein the composition is in liquid form.

34. An isolated nucleic acid encoding a modified subtilisin 309 of claim 1.

35. A vector comprising a nucleic acid of claim 34.

36. A microbial host cell comprising a vector of claim 35.

42

37. A method for producing a modified subtilisin 309, which comprises
(a) culturing a microbial host cell of claim 36 under conditions conducive to the expression and secretion of the modified subtilisin 309, and
(b) recovering the modified subtilisin 309.

38. A modified Bacillus protease PB92 comprising one or both of the following substitutions:
(a) Y167A, Y167C, Y167G, Y167H, Y167I, Y167L, Y167M, Y167N, Y167P, Y167Q, Y167S, Y167T, or Y167W, and
(b) R170A, R170C, R170F, R170G, R170H, R170L, R170N, R170P, R170S, R170T, R1 70W, or R170Y, wherein each position corresponds to a position of the amino acid sequence of subtilisin BPN'.

39. The modified Bacillus protease PB92 of claim 38, further comprising at least one further mutation at one or more of positions: 27, 36, 57, 76, 97, 101, 104, 120, 123, 206, 218, 222, 224, 235 and 274.

40. The modified Bacillus protease PB92 of claim 39, wherein at least one further mutation is selected from the group consisting of K27R, *36D, S57P, N76D, G97N, S101G, V104A, V104N, V104Y, H120D, N123S, A194P, Q206E, N218S, M222A, M222S, T224S, K235L, and T274A.

41. A detergent composition comprising a modified Bacillus protease PB92 of claim 38 and a surfactant.

42. The detergent composition of claim 41, wherein the composition is in solid powdered form.

43. The detergent composition of claim 41, wherein the composition is in liquid form.

44. An isolated nucleic acid encoding a modified Bacillus protease PB92 of claim 38.

45. A vector comprising a nucleic acid of claim 44.

46. A microbial host cell comprising a vector of claim 45.

47. A method for producing a modified Bacillus protease PB92, which comprises
(a) culturing a microbial host cell of claim 46 under conditions conducive to the expression and secretion of the modified Bacillus protease PB92, and
(b) recovering the modified Bacillus protease PB92.

48. A modified subtilisin 147 comprising one or both of the following substitutions:
(a) Y167A, Y167C, Y167G, Y167H, Y167I, Y167L, Y167M, Y167N, Y167P, Y167Q, Y167S, Y167T, or Y167W, and
(b) R170A, R170C, R170F, R170G, R170H, R170I R170L, R170M, R170N, R170P, R170S, R170T, R170V, R170W, or R170Y, wherein each position corresponds to a position of the amino acid sequence of subtilisin BPN'.

49. The modified subtilisin 147 of claim 48, further comprising at least one further mutation at one or more of positions: 27, 36, 57, 76, 97, 101, 104, 120, 123, 206, 218, 222, 224, 235 and 274.

50. The modified subtilisin 147 of claim 49, wherein at least one further mutation is selected from the group consisting of K27R, *36D, S57P, N76D, G97N, S101G, V104A, V104N, V104Y, H120D, N123S, A194P, Q206E, N218S, M222A, M222S, T224S, K235L, and T274A.

51. A detergent composition comprising a modified subtilisin 147 of claim 48 and a surfactant.

52. The detergent composition of claim 51, wherein the composition is in solid powdered form.

53. The detergent composition of claim 51, wherein the composition is in liquid form.

54. An isolated nucleic acid encoding a modified subtilisin 147 of claim 48.

55. A vector comprising a nucleic acid of claim 54.

56. A microbial host cell comprising a vector of claim 55.

57. A method for producing a modified subtilisin 147, which comprises (a) culturing a microbial host cell of claim 56 under conditions conducive to the expression and secretion of the modified subtilisin 147, and (b) recovering the modified subtilisin 147.

58. A modified subtilsin 309, comprising both of the following substitutions:

(a) Y167A, Y167C, Y167G, Y167H, Y167I, Y167L, Y167M, Y167N, Y167P, Y167Q, Y167S, Y167T, Y167V, or Y167W, and (b) R170A, R170C, R170F, R170 G, R170H, R170I, R170L, R170M, R170N, R170P, R170Q, R170S, R170T, R170V, or R170W, wherein each position corresponds to a position of the amino acid sequence of subtilsin BPN'.

59. A modified Bacillus protease PB92 comprising both of the following substitutions:

(a) Y167A, Y167C, Y167G, Y167H, Y167I, Y167L, Y167M, Y167N, Y167P, Y167Q, Y167S, Y167T, Y167V, or Y167W, and (b) R170A, R170C, R170F, R170 G, R170H, R170I, R170L, R170M, R170N, R170P, R170Q, R170S, R170T, R170V, or R170W, wherein each position corresponds to a position of the amino acid sequence of subtilsin BPN'.

60. A modified subtilsin 147, comprising both of the following substitutions:

(a) Y167A, Y167C, Y167G, Y167H, Y167I, Y167L, Y167M, Y167N, Y167P, Y167Q, Y167S, Y167T, Y167V, or Y167W, and (b) R170A, R170C, R170F, R170 G, R170H, R170I, R170L, R170M, R170N, R170P, R170Q, R170S, R170T, R170V, or R170W, wherein each position corresponds to a position of the amino acid sequence of subtilsin BPN'.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 39 nucleotides
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

AATTCAGGTG CAGGCTCAAT CAGCTATCCG GCGCTCTAT      39

(2) INFORMATION FOR SEQ ID NO: 2:

(i) SEQUENCE CHARACTERISTICS:
      (A) LENGTH: 41 nucleotides
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 2:

GTCCACGTCC GAGTTAGTCG ATAGGCCGCG AGATACGCTT G           41

(2) INFORMATION FOR SEQ ID NO: 3:

(i) SEQUENCE CHARACTERISTICS:
        (A) LENGTH: 39 nucleotides
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

AATTCAGGTG CAGGCTCAAT CAGCTATCCG GCGATCTAT              39

(2) INFORMATION FOR SEQ ID NO: 4:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GTCCACGTCC GAGTTAGTCG ATAGGCCGCT AGATACGCTT G           41

(2) INFORMATION FOR SEQ ID NO: 5:

(i) SEQUENCE CHARACTERISTICS:
        (A) LENGTH: 36 nucleotides
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

AGCTTTGTAC CAGGGGAACC GCCGACTCAA GATGGG                 36

(2) INFORMATION FOR SEQ ID NO: 6:

(i) SEQUENCE CHARACTERISTICS:
        (A) LENGTH: 38 nucleotides
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

AACATGGTCC CCTTGGCGGC TGAGTTCTAC CCTTACCC               38